US012458772B2

(12) United States Patent
Novkov

(10) Patent No.: US 12,458,772 B2
(45) Date of Patent: *Nov. 4, 2025

(54) SYSTEMS AND METHODS FOR VENTILATION HUMIDIFICATION

(71) Applicant: Covidien LP, Mansfield, MA (US)

(72) Inventor: Donald J. Novkov, Encinitas, CA (US)

(73) Assignee: Covidien LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/441,544

(22) Filed: Feb. 14, 2024

(65) Prior Publication Data

US 2024/0181197 A1 Jun. 6, 2024

Related U.S. Application Data

(63) Continuation of application No. 17/646,783, filed on Jan. 3, 2022, now Pat. No. 11,931,519, which is a (Continued)

(51) Int. Cl.
*A61M 16/14* (2006.01)
*A61M 11/00* (2006.01)
(Continued)

(52) U.S. Cl.
CPC ........ *A61M 16/147* (2014.02); *A61M 11/006* (2014.02); *A61M 16/024* (2017.08);
(Continued)

(58) Field of Classification Search
CPC .......... A61M 16/0057; A61M 16/0066; A61M 16/0833; A61M 16/0875; A61M 16/1085;
(Continued)

(56) References Cited

U.S. PATENT DOCUMENTS 3,864,544 A * 2/1975 van Amerongen ... A61M 16/16 219/214
3,987,133 A 10/1976 Andra
(Continued)

FOREIGN PATENT DOCUMENTS

CN 206325086 7/2017
CN 107106808 A 8/2017
(Continued)

OTHER PUBLICATIONS

PCT International Search Report and Written Opinion in International Application PCT/US2019/032136, mailed Aug. 23, 2019, 14 pages.
(Continued)

*Primary Examiner* — Joseph D. Boecker

(57) ABSTRACT

This disclosure describes systems and methods for humidifying ventilator delivered breathing gases. These systems and methods utilize a hollow cone atomizer (e.g., a pressure swirl atomizer) and/or a heating element associated with a heating circuit and/or a heating tube. In some aspect, the systems and methods utilize received flow, temperature, and/or humidity information to determine an amount of water to add to breathing gases to reach a desired humidity of the breathing gases delivered to the patient. In further aspects, the humidification system can serve as a nebulization system for delivering nebulized medicine.

20 Claims, 12 Drawing Sheets

Related U.S. Application Data continuation of application No. 16/411,506, filed on May 14, 2019, now Pat. No. 11,247,016.

(60) Provisional application No. 62/670,957, filed on May 14, 2018.

(51) Int. Cl.

| | |
|---|---|
| ***A61M 16/00*** | (2006.01) |
| ***A61M 16/08*** | (2006.01) |
| ***A61M 16/10*** | (2006.01) |
| ***A61M 16/16*** | (2006.01) |
| ***B05B 7/00*** | (2006.01) |

(52) U.S. Cl.

CPC .... *A61M 16/1085* (2014.02); *A61M 16/1095* (2014.02); *A61M 16/161* (2014.02); *A61M 16/162* (2013.01); *B05B 7/0075* (2013.01); *A61M 2016/0039* (2013.01); *A61M 16/0057* (2013.01); *A61M 16/0833* (2014.02); *A61M 16/0875* (2013.01); *A61M 2205/3334* (2013.01); *A61M 2205/3368* (2013.01); *A61M 2205/36* (2013.01); *A61M 2206/16* (2013.01)

(58) Field of Classification Search

CPC ............ A61M 16/1095; A61M 16/147; A61M 16/16; A61M 16/161; A61M 16/162; A61M 11/006; A61M 11/007; A61M 2016/0033; A61M 2016/0039; A61M 2205/3344; A61M 2205/3368; A61M 2205/36; A61M 2206/16; B05B 7/0075

See application file for complete search history.

(56) References Cited

U.S. PATENT DOCUMENTS

| | | | |
|---|---|---|---|
| 4,038,980 | A | 8/1977 | Fodor |
| 4,195,044 | A | 3/1980 | Miller |
| 4,572,427 | A | 2/1986 | Selfridge et al. |
| 4,701,415 | A | 10/1987 | Dutton et al. |
| 4,911,157 | A | 3/1990 | Miller |
| 4,913,140 | A | 4/1990 | Orec et al. |
| 5,062,145 | A | 10/1991 | Zwaan et al. |
| 5,226,411 | A | 7/1993 | Levine |
| 5,367,604 | A | 11/1994 | Murray |
| 5,445,143 | A | 8/1995 | Sims |
| 5,537,996 | A | 7/1996 | McPhee |
| 5,537,997 | A | 7/1996 | Mechlenburg et al. |
| 5,539,854 | A | 7/1996 | Jones et al. |
| 5,588,423 | A | 12/1996 | Smith |
| 5,616,115 | A | 4/1997 | Gloyd et al. |
| 5,640,951 | A | 6/1997 | Huddart et al. |
| 5,655,522 | A | 8/1997 | Mechlenburg et al. |
| 5,673,687 | A | 10/1997 | Dobson et al. |
| 5,769,071 | A | 6/1998 | Turnbull |
| 5,857,062 | A | 1/1999 | Bergamaschi et al. |
| 5,862,802 | A | 1/1999 | Bird |
| D418,498 | S | 1/2000 | Leonard |
| 6,019,100 | A | 2/2000 | Alving et al. |
| 6,050,260 | A | 4/2000 | Daniell et al. |
| 6,102,037 | A | 8/2000 | Koch |
| 6,135,432 | A | 10/2000 | Hebblewhite et al. |
| 6,256,454 | B1 | 7/2001 | Dykes |
| 6,338,473 | B1 | 1/2002 | Hebblewhite et al. |
| 6,349,722 | B1 | 2/2002 | Gradon et al. |
| 6,397,841 | B1 | 6/2002 | Kenyon et al. |
| 6,510,848 | B1 | 1/2003 | Gibertoni |
| 6,554,260 | B1 | 4/2003 | Lipscombe et al. |
| 6,576,358 | B2 | 6/2003 | Gebhardt et al. |
| 6,591,834 | B1 | 7/2003 | Colla et al. |
| 6,694,974 | B1 | 2/2004 | Gradon et al. |
| 6,718,974 | B1 | 4/2004 | Moberg |
| D492,399 | S | 6/2004 | Jenkinson |
| 6,745,768 | B2 | 6/2004 | Colla et al. |
| 6,802,314 | B2 | 10/2004 | McPhee |
| D498,527 | S | 11/2004 | Virr et al. |
| 6,904,911 | B2 | 6/2005 | Gibertoni |
| 6,935,337 | B2 | 8/2005 | Virr et al. |
| 6,968,841 | B2 | 11/2005 | Fini |
| 7,040,317 | B2 | 5/2006 | Colla et al. |
| 7,051,733 | B2 | 5/2006 | Gradon et al. |
| 7,096,864 | B1 | 8/2006 | Mayer et al. |
| 7,106,955 | B2 | 9/2006 | Thudor et al. |
| 7,111,624 | B2 | 9/2006 | Thudor et al. |
| 7,137,388 | B2 | 11/2006 | Virr et al. |
| 7,146,979 | B2 | 12/2006 | Seakins et al. |
| D542,900 | S | 5/2007 | Snow et al. |
| RE39,724 | E | 7/2007 | Gradon et al. |
| D549,321 | S | 8/2007 | Snow et al. |
| D549,810 | S | 8/2007 | Smith et al. |
| 7,263,994 | B2 | 9/2007 | Gradon et al. |
| D555,236 | S | 11/2007 | Snow et al. |
| D557,407 | S | 12/2007 | Lithgow et al. |
| 7,306,205 | B2 | 12/2007 | Huddart et al. |
| D559,371 | S | 1/2008 | Snow et al. |
| D559,964 | S | 1/2008 | Snow et al. |
| D561,890 | S | 2/2008 | Lithgow et al. |
| D561,891 | S | 2/2008 | Lithgow et al. |
| 7,335,157 | B2 | 2/2008 | Czupich et al. |
| D569,958 | S | 5/2008 | Snow et al. |
| 7,413,173 | B2 | 8/2008 | DiMatteo et al. |
| D576,263 | S | 9/2008 | Snow et al. |
| D579,537 | S | 10/2008 | Smith et al. |
| 7,552,730 | B2 | 6/2009 | Kates |
| 7,802,569 | B2 | 9/2010 | Yeates et al. |
| 8,074,645 | B2 | 12/2011 | Bordewick et al. |
| 8,220,463 | B2 | 7/2012 | White et al. |
| 8,333,195 | B2 | 12/2012 | Cortez, Jr. et al. |
| 8,522,782 | B2 | 9/2013 | Lewis et al. |
| 8,671,936 | B2 | 3/2014 | Meier |
| 8,720,439 | B1 | 5/2014 | Kolkowski et al. |
| 9,072,848 | B2 | 7/2015 | Bertinetti et al. |
| 9,358,358 | B2 | 6/2016 | Wondka et al. |
| 9,757,270 | B2 | 9/2017 | Carrubba |
| 9,878,120 | B2 | 1/2018 | White et al. |
| 9,925,346 | B2 | 3/2018 | Dong et al. |
| 9,980,943 | B2 | 5/2018 | Burkin |
| 10,046,128 | B2 | 8/2018 | Hill et al. |
| 10,149,952 | B2 | 12/2018 | Bertinetti et al. |
| 10,206,429 | B2 | 2/2019 | Davis et al. |
| 10,207,068 | B2 | 2/2019 | Jafari |
| 10,279,140 | B2 | 5/2019 | Winski |
| 10,362,967 | B2 | 7/2019 | Milne |
| 10,449,322 | B2 | 10/2019 | Poormand |
| 11,247,016 | B2 * | 2/2022 | Novkov .............. A61M 16/147 |
| 11,931,519 | B2 * | 3/2024 | Novkov ............ A61M 16/1085 |
| 2002/0017298 | A1 | 2/2002 | Koch |
| 2002/0083947 | A1 | 7/2002 | Seakins |
| 2002/0129815 | A1 | 9/2002 | McPhee |
| 2003/0079748 | A1 | 5/2003 | Seakins |
| 2004/0074493 | A1 | 4/2004 | Seakins et al. |
| 2004/0079370 | A1 | 4/2004 | Gradon et al. |
| 2004/0182386 | A1 | 9/2004 | Meier |
| 2004/0226561 | A1 | 11/2004 | Colla et al. |
| 2004/0229089 | A1 | 11/2004 | Preidel et al. |
| 2005/0178383 | A1 | 8/2005 | Mackie et al. |
| 2006/0037613 | A1 | 2/2006 | Kwok et al. |
| 2006/0130836 | A1 | 6/2006 | Wixey et al. |
| 2006/0137687 | A1 | 6/2006 | Colla et al. |
| 2006/0144395 | A1 | 7/2006 | Koch et al. |
| 2006/0231097 | A1 | 10/2006 | Dougherty et al. |
| 2006/0237005 | A1 | 10/2006 | Virr et al. |
| 2007/0132117 | A1 | 6/2007 | Pujol et al. |
| 2007/0157928 | A1 | 7/2007 | Pujol et al. |
| 2008/0000470 | A1 * | 1/2008 | Minocchieri ..... A61M 16/0003 128/200.21 |
| 2008/0072900 | A1 | 3/2008 | Kenyon et al. |
| 2008/0072904 | A1 | 3/2008 | Becker et al. |
| 2008/0216829 | A1 | 9/2008 | Koch et al. |
| 2008/0236577 | A1 | 10/2008 | Power |
| 2008/0302361 | A1 | 12/2008 | Snow et al. |
| 2008/0302362 | A1 | 12/2008 | Kwok |

(56) References Cited

U.S. PATENT DOCUMENTS

| | | | | |
|---|---|---|---|---|
| 2009/0000620 | A1 | 1/2009 | Virr | |
| 2016/0228282 | A1 | 8/2016 | Carrubba | |
| 2016/0243324 | A1 | 8/2016 | Doyle | |
| 2016/0250427 | A1 | 9/2016 | Jafari | |
| 2016/0256643 | A1 | 9/2016 | Graboi | |
| 2016/0256656 | A1 | 9/2016 | Glenn | |
| 2016/0354566 | A1 | 12/2016 | Thiessen | |
| 2017/0095627 | A1 | 4/2017 | Jafari | |
| 2017/0164872 | A1 | 6/2017 | Sanborn | |
| 2017/0182269 | A1 | 6/2017 | Masic | |
| 2017/0296765 | A1 | 10/2017 | Dong | |
| 2018/0036500 | A1 | 2/2018 | Esmaeil-Zadeh-Azar | |
| 2018/0193578 | A1 | 7/2018 | Glenn | |
| 2018/0207378 | A1 | 7/2018 | Masic | |
| 2018/0207379 | A1 | 7/2018 | Masic | |
| 2018/0250490 | A1 * | 9/2018 | Burgess | A61M 16/16 |
| 2018/0325459 | A1 | 11/2018 | Nakai | |
| 2022/0072263 | A1 * | 3/2022 | Novkov | A61M 16/16 |

FOREIGN PATENT DOCUMENTS

| | | | | |
|---|---|---|---|---|
| FR | 2966048 | | 4/2015 | |
| WO | WO-2005079898 | A2 * | 9/2005 | A61M 11/044 |
| WO | 2012080923 | | 6/2012 | |
| WO | 2015/033288 | A1 | 3/2015 | |
| WO | 2016/036260 | A1 | 3/2016 | |
| WO | 2017/131966 | A1 | 8/2017 | |

OTHER PUBLICATIONS

Chen et al., "Influence of Geometric Features on the Performance of Pressure-Swirl Atomizers", Journal of Engineering for Gas Turbines and Power, Oct. 1990, vol. 112, pp. 579-582.

Rizk, N.K. et al., "Influence of Liquid Properties on the Internal Flow Characteristics of Simplex Swirl Atomizers" Atomization and Spray Technology 2 (1986), pp. 219-232.

Chen, S.K. et al., "Factors Influencing the Effective Spray Cone Angle of Pressure-Swirl Atomizers" Journal of Engineering for Gas Turbines and Power, Jan. 1992, vol. 114, pp. 97-103.

Dodge, L.G. et al., "Effect of Elevated Temperature and Pressure on Sprays From Simplex Swirl Atomizers", Journal of Engineering for Gas Turbines and Power, Jan. 1986, vol. 108, pp. 209-215.

Zhao, Y.H. et al., "Experimental and Analytical Investigation on the Variation of Spray Characteristics Along Radial Distance Downstream of a Pressure Swirl Atomizer", Journal of Engineering for Gas Turbines and Power, Jan. 1986, vol. 108, pp. 473-478.

Babu, K. Ranganadha, et al., "Design of Swirl Chamber Atomisers", International Conference on Liquid Atomisation & Spray Systems, V1, 1985, pp. 1-7.

Chin, J.S. et al., "Influence of Downstream Distance on the Spray Characteristics of Pressure-Swirl Atomizers", Journal of Engineering for Gas Turbines and Power, Jan. 1986, vol. 108, pp. 219-224.

Spalding, D. Brian, "Computational Fluid Dynamics and Its Application to Liquid-Atomisation and Spray Systems", International Conference on Liquid Atomisation & Spray Systems, V2, 1985, pp. 1-6.

Rizk, N.K. et al., "Prediction of Velocity Coefficient and Spray Cone Angle for Simplex Swirl Atomizers", International Conference on Liquid Atomisation & Spray Systems, V1, 1985, pp. 1-16.

Doble, S. M., "Design of Centrifugal Spray Nozzles for Outputs up to 1,800 gallons per hour", Proceedings of the Institute of Mechanical Engineers, vol. 157 (1947), pp. 103-119.

Zhao, Y.H. et al., "Dropsize Distributions from Swirl and Airblast Atomizers", Atomization and Spray Technology 2, 1986, pp. 3-15.

7200 Series Ventilator, Options, and Accessories: Operator's Manual. Nellcor Puritan Bennett, Part No. 22300 A, Sep. 1990, pp. 1-196.

7200 Ventilatory System: Addendum/Errata. Nellcor Puritan Bennett, Part No. 4-023576-00, Rev. A, Apr. 1998, pp. 1-32.

800 Operator's and Technical Reference Manual. Series Ventilator System, Nellcor Puritan Bennett, Part No. 4-070088-00, Rev. L, Aug. 2010, pp. 1-476.

840 Operator's and Technical Reference Manual. Ventilator System, Nellcor Puritan Bennett, Part No. 4-075609-00, Rev. G, Oct. 2006, pp. 1-424.

Puritan Bennett 980 Series Ventilator Operator's Manual, Covidien, Jan. 29, 2014, Part. No. 10077893 A Jan. 2014, 506 pages.

Chinese Office Action for CN Application No. 201980032217.1 mailed May 5, 2022 (10 pages).

* cited by examiner

SYSTEMS AND METHODS FOR VENTILATION HUMIDIFICATION

CROSS-REFERENCE TO RELATED APPLICATIONS

This application is a continuation of U.S. application Ser. No. 17/646,783, filed Jan. 3, 2022, which is a continuation of U.S. application Ser. No. 16/411,506, filed 14 May 2019, now Issued U.S. Pat. No. 11,247,016 which claims the benefit of U.S. Provisional Application Ser. No. 62/670,957, filed 14 May 2018, and which applications are incorporated herein by reference. To the extent appropriate, a claim of priority is made to each of the above-disclosed applications.

BACKGROUND

Medical ventilator systems have long been used to provide ventilatory and supplemental oxygen support to patients. These ventilators typically comprise a source of pressurized oxygen which is fluidly connected to the patient through a conduit or tubing. Some ventilators are used with humidifiers to humidify the gas delivered to the patient to improve patient adherence and comfort.

SUMMARY

This disclosure describes systems and methods for humidifying ventilator delivered breathing gas. The disclosure describes a novel humidification system that utilizes an atomizer and a heating element. For example, the atomizer may be a hollow cone atomizer (e.g., such as a pressure swirl atomizer). Traditionally, pressure swirl atomizers are used to inject water upstream of a turbine of a high performance jet engine to provide a temporary boost in thrust as water increases gas density across the turbine. Such pressure swirl atomizers generally comprise more than one inlet channel into a swirl chamber, as will be described further below. In some aspects, the disclosure describes a novel humidification system that utilizes received flow, humidity, and/or temperature information to determine the amount of water to add to the breathing gas to obtain a desired percentage of relative humidity, as well as regulating a temperature, of the breathing gases delivered to the patient. In further aspects, the humidification system can serve as a nebulization system for delivering nebulized medicine. In a first example, a water-soluble medicine may be added to the water and the combination of water and medicine may be atomized and delivered to the breathing gases by the atomizer. In a second example, a second atomizer designed for the fluid characteristics of different medicines may be integrated into the humidifier (or provided as a removable plug-in device to the humidifier) for delivering nebulized medicines into breathing gases.

In an aspect, a method for humidifying ventilator delivered breathing gases is provided. The method includes receiving, at a humidifier, inspiratory flow information about breathing gases upstream of an atomizer of the humidifier and measuring, by the humidifier, humidity information for the breathing gases upstream of the atomizer. The method further includes calculating, based on the inspiratory flow information and the humidity information, an amount of water to add to the breathing gases to reach a desired humidity and delivering, via the atomizer, the amount of water in bursts of atomized water directly into a flow path of the breathing gases. Additionally, the method includes vaporizing the atomized water upon contact of the water with a heating tube in the flow path downstream of the atomizer to form humidified breathing gases and delivering the humidified breathing gases to a ventilation tubing system for delivery to a patient being ventilated by the ventilator.

In another aspect, a humidifier that provides humidification to breathing gases for ventilating a patient is provided. The humidifier includes a first sensor that monitors an inspiratory flow of breathing gases upstream of an atomizer of the humidifier and a second sensor that monitors humidity information of the breathing gases upstream of the atomizer. The humidifier further includes a processor that calculates, based on the inspiratory flow and the humidity information, an amount of water to add to the breathing gases to reach a desired humidity. Additionally, the humidifier includes a controller that commands the atomizer to deliver the amount of water in bursts of atomized water directly into a flow path of the breathing gases and commands a heating element to heat a thermally-conductive material in the flow path downstream of the atomizer, wherein the atomized water is vaporized upon contact of the water with the thermally-conductive material to form humidified breathing gases for delivery to a patient being ventilated by the ventilator.

In yet another aspect, a humidifier that provides humidification to breathing gases for ventilating a patient is provided. The humidifier includes a sensor that monitors humidity information of the breathing gases upstream of the atomizer, a controller that receives an inspiratory flow of the breathing gases upstream of the humidifier, and a processor that calculates, based on the inspiratory flow and the humidity information, an amount of water to add to the breathing gases to reach a desired humidity. The humidifier further includes the atomizer commanded by the controller to deliver the amount of water in bursts of atomized water directly into a flow path of the breathing gases and a heating element commanded by the controller to heat a thermally-conductive material in the flow path downstream of the atomizer, wherein the atomized water is vaporized upon contact of the water with the thermally-conductive material to form humidified breathing gases for delivery to a patient being ventilated by the ventilator.

These and various other features as well as advantages which characterize the systems and methods described herein will be apparent from a reading of the following detailed description and a review of the associated drawings. Additional features are set forth in the description which follows, and in part will be apparent from the description, or may be learned by practice of the technology. The benefits and features of the technology will be realized and attained by the structure particularly pointed out in the written description and claims hereof as well as the appended drawings.

It is to be understood that both the foregoing general description and the following detailed description are exemplary and explanatory and are intended to provide further explanation of the present disclosure as claimed.

BRIEF DESCRIPTION OF THE DRAWINGS

The following drawing figures, which form a part of this application, are illustrative of aspects of systems and methods described below and are not meant to limit the scope of the disclosure in any manner, which scope shall be based on the claims appended hereto.

DETAILED DESCRIPTION

Figure 1:
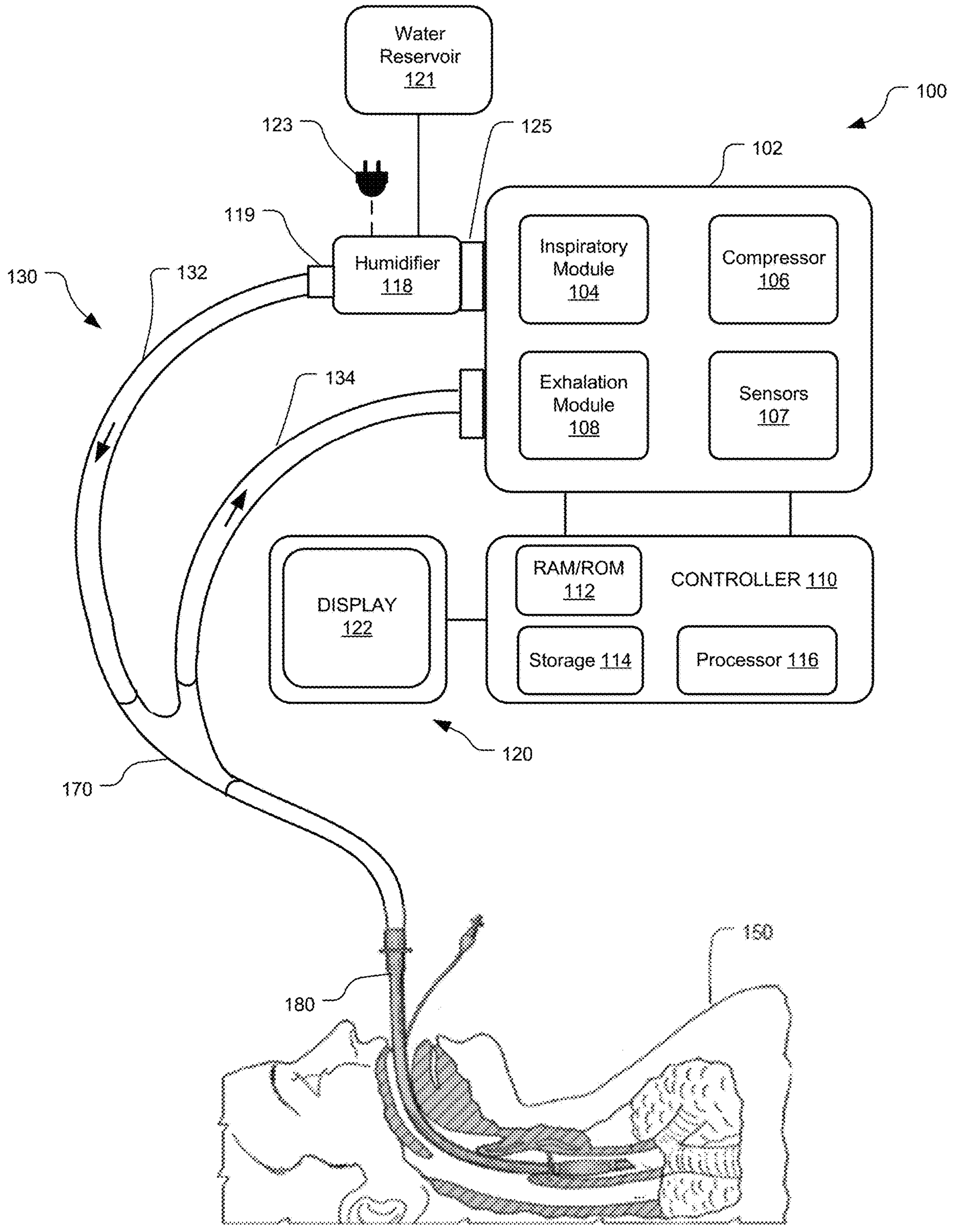
FIG. 1 is schematic diagram illustrating a first aspect of a ventilator ventilating a patient with a humidifier including an atomizer and a heating tube, in accordance with aspects of the disclosure.

Although the techniques introduced above and discussed in detail below may be implemented for a variety of medical devices, the present disclosure will discuss the implementation of these techniques in the context of a medical ventilator for use in providing ventilation support to a human patient. A person of skill in the art will understand that the technology described in the context of a medical ventilator for human patients could be adapted for use with other systems such as ventilators for non-human patients and general gas transport systems.

Medical ventilators are used to provide breathing gases to a patient who may otherwise be unable to breathe sufficiently. In modern medical facilities, pressurized air and oxygen sources are often available from wall outlets. Accordingly, ventilators may provide pressure regulating valves (or regulators) connected to centralized sources of pressurized air and pressurized oxygen. The regulating valves function to regulate flow so that respiratory gases having a desired concentration of oxygen are supplied to the patient at desired pressures and rates. Ventilators capable of operating independently of external sources of pressurized air are also available.

While operating a ventilator, it is desirable to control the percentage of oxygen in the gases supplied by the ventilator to the patient. Further, some ventilators are used with humidifiers to humidify the breathing gases delivered to the patient to improve patient adherence and comfort. However, currently utilized humidifiers often over humidify the delivered breathing gases leading to an accumulation of water in the patient circuit, referred to herein as "rainout." The accumulated water in the patient circuit can interfere with circuit sensors and/or filters and can increase the chances of patient infection, such as pneumonia. Accordingly, the accumulated water must be removed or cleared from the patient circuit. As such, over humidification leading to rainout is problematic with current ventilator humidifiers. Under humidification is also problematic, particularly in low-gas flow ventilator operating conditions, because under humidification for prolonged periods can result in airway damage due to dryness and other patient harm.

Accordingly, the current disclosure describes systems and methods for humidifying ventilator delivered breathing gases that reduces and/or prevents rainout. The systems and methods as described herein utilize a hollow cone atomizer and a heating system. The heating system may comprise a heating element associated with a heating tube or a heating circuit. Further, in some aspects, the system and methods as described herein utilize received flow, temperature, and/or humidity information to determine the amount of water to add to the breathing gases to obtain a desired percentage of relative humidity, as well as regulating temperature, in the breathing gases delivered to the patient. In aspects, the humidifier may incorporate an atomizer (e.g., a hollow cone or full cone atomizer) to disperse the determined amount of water into small droplets that are more easily vaporized and diffused into the breathing gases. The humidifier may be integrated into or used as a standalone device with invasive or non-invasive ventilation, a home CPAP system, and even "high flow" systems for use with nasal cannulas, masks, and/or helmets.

Flow, temperature, and/or humidity information may be measured by one or more sensors located internally (e.g., at or near the inspiratory and/or exhalation modules of the ventilator), externally (e.g., integrated into the humidifier, integrated into the patient circuit or wye fitting, or integrated into a probe in communication with the humidifier), or combinations thereof. Accordingly, the systems and methods disclosed herein reduce or prevent rainout in the patient circuit, reduce and/or prevent over or under humidification, can utilize less water resulting in less filter saturation, and can utilize a heating element having minimal warm-up time, either in proximity to the humidifier or integrated into the ventilatory tubing system. In some aspects, the use of a heating tube or a heating inspiratory limb can further minimize the need to heat the exhalation limb; in other aspects, both the inspiratory limb and the exhalation limb may be heated.

In further aspects, the humidification system can serve as a nebulization system for delivering nebulized medicine. In a first example, a water-soluble medicine may be added to the water and the combination of water and medicine may be vaporized and delivered to the breathing gases by the humidifier described herein. In a second example, a second atomizer designed for the fluid characteristics of different medicines may be integrated into the humidifier (or provided as a removable plug-in device to the humidifier) for delivering nebulized medicines into breathing gases.

FIG. 1 is a diagram illustrating a first aspect of an exemplary ventilator 100 connected to a human patient 150. Ventilator 100 includes a pneumatic system 102 (also referred to as a pressure generating system 102) for circulating breathing gases to and from patient 150 via the ventilation tubing system 130, which couples the patient 150 to the pneumatic system 102 via a patient interface 180, which may be an invasive patient interface (e.g., endotracheal tube, as shown) or a non-invasive patient interface (e.g., nasal mask or nasal prongs, not shown).

Ventilation tubing system 130 (or patient circuit 130) may be a two-limb (shown) or a one-limb circuit for carrying gases to and from the patient 150. In a two-limb aspect, a fitting, typically referred to as a "wye-fitting" 170, may be provided to couple the patient interface 180 to an inspiratory limb 132 and an expiratory limb 134 of the ventilation tubing system 130.

Pneumatic system 102 may be configured in a variety of ways. In the present example, pneumatic system 102 includes an exhalation module 108 coupled with the exhalation limb 134 and an inspiratory module 104 coupled with the inspiratory limb 132. Compressor 106 or other source(s) of pressurized gases (e.g., air, oxygen, and/or helium) is coupled with inspiratory module 104 to provide a gas source for ventilatory support via inspiratory port 125 to inspiratory limb 132. The inspiratory module 104 is configured to deliver breathing gases to the patient 150 according to prescribed ventilatory settings. In some aspects, inspiratory module 104 is configured to provide ventilation according to various breath types, e.g., via volume-control, pressure-control, proportional assist control, or via any other suitable breath types. The exhalation module 108 is configured to release gases from the patient's lungs according to prescribed ventilatory settings. Specifically, exhalation module 108 is associated with and/or controls an exhalation valve for releasing gases from the patient 150.

The ventilator 100 may also include one or more sensors 107 communicatively coupled to ventilator 100. The sensors 107 may be located in the pneumatic system 102, ventilation tubing system 130, and/or on the patient 150. FIG. 1 illustrates an example of a sensor 107 in pneumatic system 102. Sensors 107 may communicate with various components of ventilator 100, e.g., pneumatic system 102, other sensors 107, processor 116, humidifier 118, heating tube 119, and/or any other suitable components and/or modules. A module as used herein refers to memory, one or more processors, storage, and/or other components of the type commonly found in command and control computing devices.

In one aspect, sensors 107 generate output and send this output to pneumatic system 102, other sensors 107, processor 116, controller 110, humidifier 118, heating element of heating tube 119, and/or any other suitable components and/or modules. Sensors 107 may employ any suitable sensory or derivative technique for monitoring one or more patient parameters or ventilator parameters associated with the ventilation of a patient 150. Sensors 107 may detect changes in patient parameters indicative of patient triggering, for example. In other examples, the sensor 107 may include a humidity sensor, a temperature sensor, a combined temperature/humidity sensor, and/or inspiratory flow sensor. In some aspects, the humidity sensor determines the humidity and temperature of the breathing gas. In other aspects, the inspiratory flow sensor determine the inspiratory flow rate of the breathing gas.

Sensors 107 may be placed in any suitable location, e.g., within the ventilatory circuitry or other devices communicatively coupled to the ventilator 100. Further, sensors 107 may be placed in any suitable internal location, such as, within the ventilatory circuitry or within components or modules of ventilator 100. For example, sensors 107 may be coupled to the inspiratory and/or exhalation modules for detecting changes in, for example, circuit pressure and/or flow. In other examples, sensors 107 may be affixed to the ventilatory tubing or may be embedded in the tubing itself. According to some aspects, sensors 107 may be provided at or near the lungs (or diaphragm) for detecting a pressure in the lungs. Additionally or alternatively, sensors 107 may be affixed or embedded in or near wye-fitting 170 and/or patient interface 180. Indeed, any sensory device useful for monitoring changes in measurable parameters during ventilatory treatment may be employed in accordance with aspects described herein.

As should be appreciated, with reference to the Equation of Motion, ventilatory parameters are highly interrelated and, according to aspects, may be either directly or indirectly monitored. That is, parameters may be directly monitored by one or more sensors 107, as described above, or may be indirectly monitored or estimated/calculated using a model, such as a model derived from the Equation of Motion:

$$\text{Target Airway Pressure}(t)=E_p\int Q_p\,dt+Q_pR_p-\text{Patient Effort}(t)$$

The pneumatic system 102 may include a variety of other components, including mixing modules, valves, tubing, accumulators, filters, humidifier 118, heating tube 119, water reservoir 121, etc. In other aspects, these other components are located outside of the pneumatic system 102, such as the mixing modules, valves, tubing, accumulators, filters, humidifier 118, heating tube 119, water reservoir 121, etc.

Controller 110 is operatively coupled with pneumatic system 102, signal measurement and acquisition systems, and an operator interface 120 that may enable an operator to interact with the ventilator 100 (e.g., change ventilator settings, select operational modes, view monitored parameters, etc.). In some aspects, the controller in electronic communication with and/or operatively coupled to a humidifier 118 and/or a heating tube 119. For example, the controller 110 of the ventilator 100 may send an inspiratory flow command, inspiratory flow measurements, and/or temperature or humidity measurements of the breathing gases to the humidifier 118 and/or a heating tube 119.

In one aspect, the operator interface 120 of the ventilator 100 includes a display 122 communicatively coupled to ventilator 100. Display 122 provides various input screens, for receiving clinician input, and various display screens, for presenting useful information to the clinician. In one aspect, the display 122 is configured to include a graphical user interface (GUI). The GUI may be an interactive display, e.g., a touch-sensitive screen or otherwise, and may provide various windows and elements for receiving input and interface command operations. Alternatively, other suitable means of communication with the ventilator 100 may be provided, for instance by a wheel, keyboard, mouse, or other suitable interactive device. Thus, operator interface 120 may accept commands and input through display 122. Display 122 may also provide useful information in the form of various ventilatory data regarding the physical condition of a patient 150. The useful information may be derived by the ventilator 100, based on data collected by a processor 116, and the useful information may be displayed to the clinician in the form of graphs, wave representations, pie graphs, text, or other suitable forms of graphic display. For example, patient data may be displayed on the GUI and/or display 122. Additionally or alternatively, patient data may be communicated to a remote monitoring system coupled via any suitable means to the ventilator 100. In one aspect, the display 122 may display one or more of a flow rate, a relative humidity of the breathing gases, a temperature of the breathing gases, a selected breath type, a humidifier on or a humidifier off status, etc.

Controller 110 may include memory 112, one or more processors 116, storage 114, and/or other components of the type commonly found in command and control computing devices. The memory 112 includes non-transitory, computer-readable storage media that stores and/or encodes software (such as computer executable instruction) that is executed by the processor 116 and which controls the operation of the ventilator 100. In an aspect, the memory 112 includes one or more solid-state storage devices such as flash memory chips. In an alternative aspect, the memory 112 may be mass storage connected to the processor 116 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 116. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

As illustrated by FIG. 1, the ventilator 100 also includes a humidifier 118 located upstream or directly upstream of heating tube 119. In some aspects, the humidifier 118 includes the heating tube 119 (not shown); while in other aspects, the heating tube 119 is separate from and independent of the humidifier 118 (as shown). In aspects, as illustrated by FIG. 1, humidifier 118 may be a stand-alone device, including a controller and processors for monitoring and regulating humidity of the breathing gases, as well as including an independent gas flow sensor. In this case, humidifier 118 may be installed outside of the ventilator 100 near inspiratory port 125 and may be independently powered via power interface 123. In other aspects (not shown), humidifier 118 including heating tube 119 may be utilized in conjunction with a heating circuit (such as heating circuit 230). In some aspects, illustrated by FIGS. 3 and 4, humidifier 118 may be integrated with the ventilator 100, may include a controller and processors for monitoring and regulating humidity of the breathing gases, but may not include an independent gas flow sensor. In still other aspects, humidifier 118 may be integrated with and controlled by ventilator 100 via controller 110, may not comprise an independent gas flow sensor, and may also be powered by ventilator 100 (not shown). Whether the humidifier 118 is integrated with the ventilator or is a stand-alone device, the humidifier 118 may access a water supply via water reservoir 121, which may be independent of (as shown) or integrated with ventilator 100. Additionally, the water supply accessed by humidifier 118 may be filtered by a water filter (not shown). In some cases, a medicine may be dissolved in the water supply, e.g., where the water supply is an intravenous (IV) bag.

Heating tube 119 may form a short conduit (e.g., two to five inches long) downstream of humidifier 118 (shown) and upstream of inspiratory limb 132. Alternatively, heating tube 119 may be integrated into humidifier 118 (not shown) and may form a short conduit upstream of inspiratory limb 132. As noted above and illustrated in FIG. 2, heating tube 119 may form a short conduit upstream of heating inspiratory limb 232 (not shown). Heating tube 119 may comprise a thermally-conductive material, such as aluminum, silver, copper, or other suitable metal or alloy (which, in some cases may be thinly plated with nickel to prevent corrosion), and a heating element. In some aspects, the heating element may be a heater blanket surrounding the thermally conductive material of heating tube 119. The heating element may generate thermal energy via any suitable means, e.g., electrical, chemical, or otherwise, and may deliver the thermal energy to the thermally-conductive material via any suitable means (e.g., via an external sleeve or blanket, internal or external wiring, etc.). In aspects, the heating element may heat quickly, e.g., in less than one minute, and may be controlled by humidifier 118 and/or ventilator 100 to achieve a desired temperature. As illustrated, heating tube 119 is in fluid communication with the inspiratory limb 132 of the ventilation tubing system 130. In this way, heating tube 119 contacts air or liquid in the flow path for maintaining a desired humidity of the breathing gases and preventing rainout in the ventilation tubing system 130. In some aspects, a second heating tube (not shown) may be placed on the exhalation side of the wye fitting 170 in order to maintain a desired humidity of exhaled gases and to prevent rainout in the exhalation limb 134 of the ventilation tubing system 130.

In some aspects, the humidifier 118 also includes a controller (similar to controller 110) with a memory (similar to memory 112), one or more processors (similar to processors 116), storage (similar to storage 114), a display (similar to display 122) and/or other components of the type commonly found in command and control computing devices similar to the ones described above for the ventilator 100. In some cases, when humidifier 118 includes one or more of the above-described components of command and control computing devices, the humidifier 118 may be integrated with ventilator 100; in other cases, the humidifier 118 may be a stand-alone unit that is communicatively coupled to ventilator 100. As used herein, communicatively or operatively coupled refers to any wired or wireless communication infrastructure configured for receiving and/or transmitting commands, data, measurements, or other information. In some cases, whether the humidifier 118 is integrated with the ventilator 100 or is a stand-alone unit, the humidifier may be independently powered via power interface 123.

When humidifier 118 includes one or more of the above-described components of command and control computing devices (not shown), the humidifier memory includes non-transitory, computer-readable storage media that stores and/or encodes software (such as computer executable instruction) that is executed by the humidifier processor and which controls the operation of the humidifier 118. In an aspect, the humidifier memory includes one or more solid-state storage devices such as flash memory chips. In an alternative aspect, the humidifier memory may be mass storage connected to the humidifier processor through a mass storage controller (not shown) and a communications bus (not shown). Although the description of computer-readable media contained herein refers to a solid-state storage, it should be appreciated by those skilled in the art that computer-readable storage media can be any available media that can be accessed by the humidifier processor. That is, computer-readable storage media includes non-transitory, volatile and non-volatile, removable and non-removable media implemented in any method or technology for storage of information such as computer-readable instructions, data structures, program modules or other data. For example, computer-readable storage media includes RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by the computer.

Figure 2:
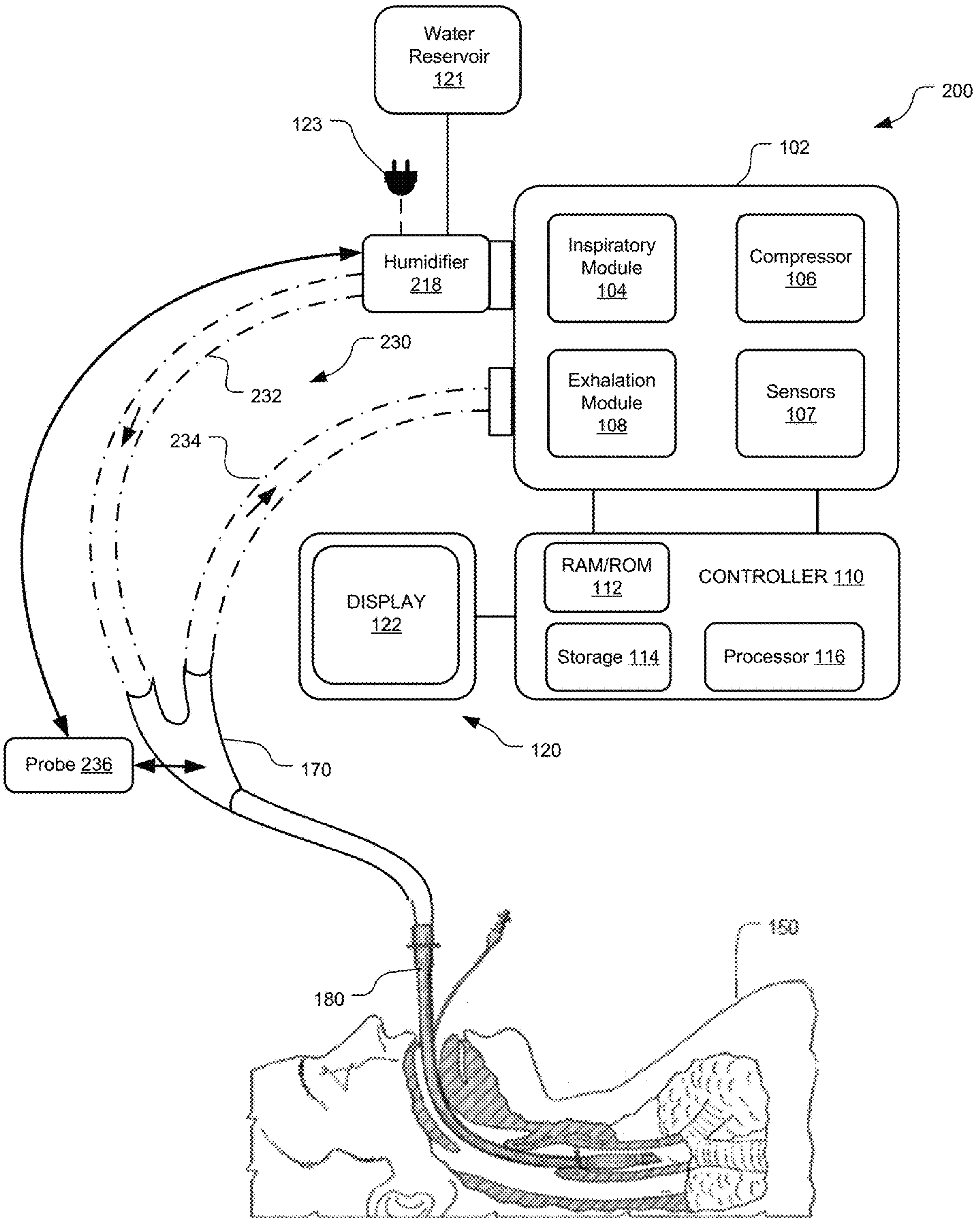
FIG. 2 is schematic diagram illustrating a second aspect of a ventilator ventilating a patient with a humidifier including an atomizer, a probe, and a heating circuit, in accordance with aspects of the disclosure.

FIG. 2 is a diagram illustrating a second aspect of an exemplary ventilator 200 connected to a human patient 150. Similar to ventilator 100, ventilator 200 includes a pneumatic system 102 for circulating breathing gases to and from patient 150 via a ventilation tubing system, which couples the patient 150 to the pneumatic system 102 via a patient interface 180 (e.g., endotracheal tube, as shown). Other than the components described below, the components of ventilator 200 are similarly described to the components of ventilator 100. Similar to ventilator 100, ventilator 200 is communicatively coupled to a humidifier 218. However, in the second aspect illustrated by FIG. 2, humidifier 218 does not comprise heating tube 119 but is communicatively coupled to a heating circuit 230 and/or a probe 236.

Heating circuit 230 may comprise a heating inspiratory limb 232 and/or a heating exhalation limb 234. Unlike heating tube 119, which is in contact with a minimal portion of a patient circuit, heating circuit 230 may comprise a heating element (depicted by dashed lines) that is in contact with a substantial portion of the patient circuit, including a heating inspiratory limb 232 and/or a heating exhalation limb 234. The heating element may be independent and may surround (e.g., as a heater blanket) a traditional, disposable patient circuit to form heating circuit 230. In this case, the heating element may be non-disposable and capable of sterilization between patients; or the heating element may itself be disposable. Alternatively, the heating element may be integrated (e.g., wired) into a custom, disposable patient circuit to form heating circuit 230. The heating element may generate thermal energy via any suitable means, e.g., electrical, chemical, or otherwise, and may deliver the thermal energy to heat the patient circuit via any suitable means (e.g., via an external sleeve or blanket, internal or external wiring, etc.). In aspects, the heating element may heat quickly, e.g., in one minute or less, and may be controlled by humidifier 218, probe 236, and/or ventilator 100 to achieve a desired temperature.

As illustrated, heating circuit 230 comprises heating inspiratory limb 232 (depicted by dashed lines) and heating exhalation limb 234 (depicted by dashed lines) and is in substantial fluid communication with breathing gases and exhalation gases to regulate humidity and prevent rainout in heating circuit 230. The purpose of heating the inspiratory limb is to heat the humidified breathing gases in order to control a temperature of the breathing gases at the wye fitting (e.g., between 32 and 42 degrees C.), to provide further evaporative heating power (or to provide all of the evaporative heating power required to vaporize the injected water when the humidifier does not include a heating tube), and to prevent condensation of water on the inside walls of the inspiratory limb. The purpose of heating the exhalation limb is to heat exhalation gases to prevent condensation from forming on the inside walls, so the temperature in the heating exhalation limb 234 should be maintained at a level just above the dew point of the exhaled gases (for example maintained at 44 degrees C.). Alternatively, heating circuit 230 may comprise heating inspiratory limb 232 without heating exhalation limb 234. In this case, heating inspiratory limb 232 may regulate temperature of the humidified breathing gases and may prevent rainout in the heating inspiratory limb 232 as well as minimizing rainout the non-heated exhalation limb 134 (not shown).

Probe 236 may be communicatively coupled to or integrated into wye fitting 170 (depicted by a two-way arrow). In one example, probe 236 comprises a temperature sensor and/or humidity sensor (not shown) for monitoring the temperature and/or humidity of the constituents (e.g., breathing gas and water) flowing through heating circuit 230. In another example, probe 236 is communicatively coupled to a temperature sensor and/or humidity sensor (not shown) associated with the wye fitting 170 for monitoring the temperature and/or humidity of the constituents (e.g., breathing gas and water) flowing through heating circuit 230. The temperature and/or humidity sensor is similar to temperature and/or humidity sensor 107, as described above. In further aspects, probe 236 is communicatively coupled to humidifier 118 (depicted by a two-way arrow) and may provide feedback to humidifier 218 regarding the temperature and/or humidity of breathing gases flowing to patient 150 and/or exhalation gases flowing back to the ventilator 200. Based on the feedback from probe 236, humidifier 218 may adjust an amount of water delivered to the flow path and/or may adjust an amount of heat delivered by the heating element to heating circuit 230.

Figure 3:
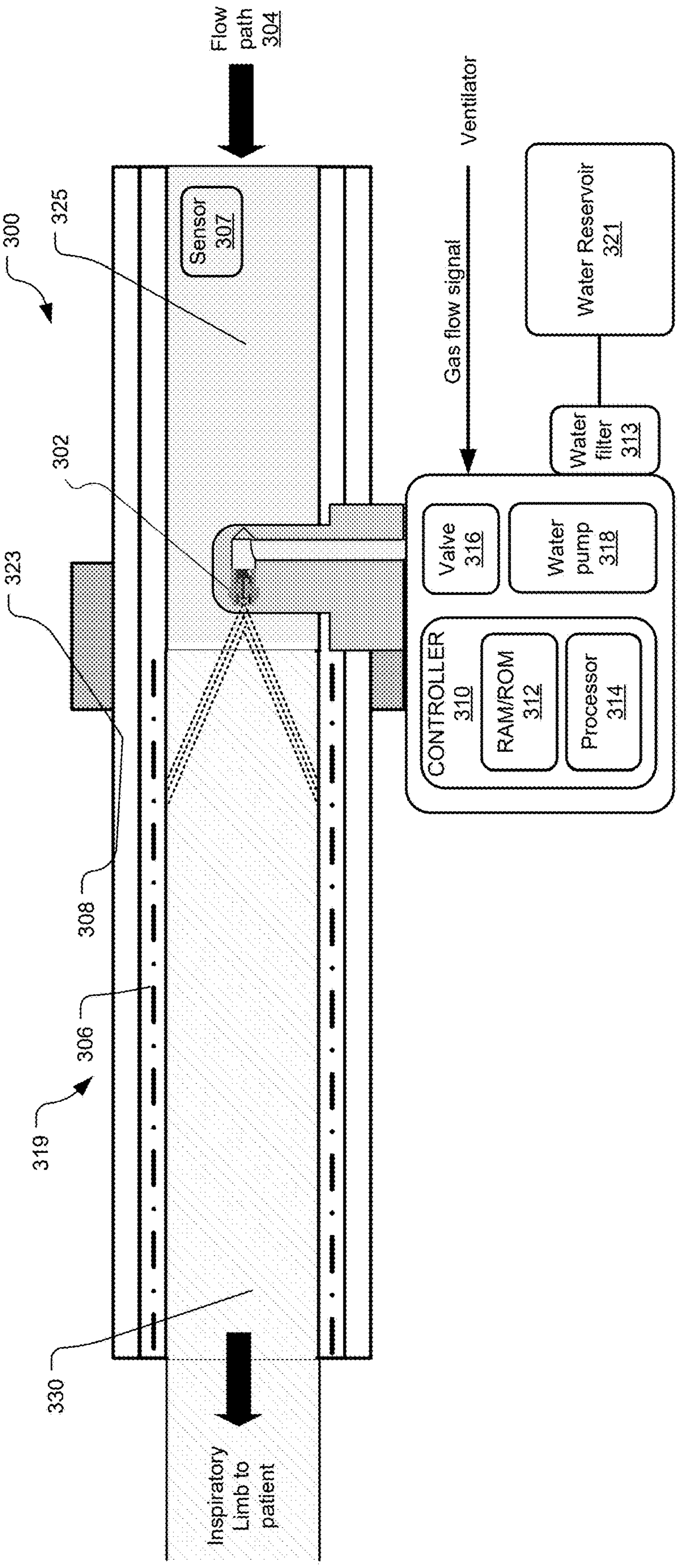
FIG. 3 is a partial, cross-sectional schematic diagram illustrating a first aspect of a humidifier including a hollow cone atomizer in a flow path of a ventilator during ventilation of a patient, in accordance with aspects of the disclosure.

FIG. 3 is a partial cross-sectional schematic diagram illustrating a first aspect of a humidifier 300 (similar to humidifier 118 or humidifier 218, detailed above) including a hollow cone atomizer 302 in a flow path 304 of a ventilator (similar to ventilator 100 or ventilator 200, detailed above) during ventilation of a patient 150, in accordance with aspects of the disclosure. As illustrated, humidifier 300 does not comprise a gas flow sensor and is integrated with the ventilator (e.g., ventilator 100 or ventilator 200). As with humidifier 118, humidifier 300 comprises a heating tube 319 (similar to heating tube 119). While humidifier 300 is not shown in fluid communication with a heating inspiratory limb (e.g., such as heating inspiratory limb 232), this configuration is contemplated and humidifier 300 may easily be implemented in such a system. In aspects, the hollow cone atomizer 302 may be a pressure swirl atomizer. As illustrated, the hollow cone atomizer 302 is positioned to spray water (or water and medicine) directly into the flow path 304 of the breathing gases, which gases may exhibit variable initial humidity levels. For instance, if the breathing gas source is dry, such as from bottled gases, hospital wall gases, or gases from a compressor with dryer, then a greater amount of water would need to be injected into the breathing gas stream than would be the case, for example, if the breathing gas source is from a blower-based system that provides gases at an ambient humidity level. As humidifier 300 is integrated with the ventilator, the flow path 304 is within the pressure generating system 102. Alternatively, where the humidifier is a stand-alone device, the flow path may be downstream from the pressure generating system 102 but upstream from the ventilator tubing system 130, as illustrated in FIG. 1.

In some aspects, a second atomizer (not shown) may be provided in the flow path 304 passing through the humidifier 300. In this case, the second atomizer may be designed based on the fluid characteristics of a medicine or medicines to be delivered. For instance, when medicines are not water-soluble, these medicines may be significantly more viscous than water, and therefore the dimensions of the atomizer may need to be adjusted to appropriately atomize the medicine. Depending on the fluid characteristics, this second atomizer may be a more conventional (non-pressure swirl) atomizer type. The second atomizer may use the same type of reservoir, pumping and valve system, as described below. Alternatively, depending on the fluid characteristics of the medicine, the second atomizer may require adjustments to the reservoir, pumping, and/or valve system as appropriate for the fluids and the pressures used. In aspects, a medicine dissolved in a biologically-compatible solvent is delivered to the second atomizer via a suitable valve and/or pumping system. Similar to the first atomizer, the second atomizer disperses the medicine-solvent solution in small droplets into the flow path. Depending on the location of the second atomizer with respect to the heated tube 319, and the fluid characteristics of the medicine-solvent solution, the small droplets may or may not be vaporized by the humidifier 300. However, it is contemplated that small droplets of the medicine-solvent may deliver a prescribed amount of the medicine to the breathing gases without requiring vaporization. While the second atomizer could be located before or after the first atomizer (e.g., atomizer 302), the preferred location is downstream of the first atomizer and the heated tube 319. In some cases, the second atomizer may be a removable plug-in device, e.g., connected via an access port in the humidifier housing that may be covered when not in use.

In some aspects, the humidifier 300 also includes a water reservoir 321, a high-pressure water pump 318 and a valve 316, which are in fluid communication with the hollow cone atomizer 302. For example, the water pump 316 pumps water from the water reservoir 321 towards the hollow cone atomizer 302 through valve 316. The water reservoir 321, such as an intravenous (IV) bag of distilled water or other suitable water supply, supplies water at ambient pressure to the water pump 318. In some cases, a medication may be dissolved in the water reservoir 321, e.g., dissolved in the intravenous (IV) bag. An outlet of the water pump 318 is directed to the valve 316. In some aspects, the valve 316 is a fast-response solenoid valve that delivers high-pressure water to the hollow cone atomizer 302.

As illustrated, humidifier 300 further includes a controller 310 including memory 312 and at least one processor 314. Controller 310 may be operative to receive an inspiratory flow command from the ventilator (e.g., ventilator 100) and may command valve 316 to deliver an amount of water sufficient to maintain a user-selected relative humidity of the breathing gases. In further aspects, the controller 310 may command valve 316 to deliver an amount of water including a dissolved or suspended medicine. In this case, the amount of water may be calculated to be sufficient to maintain the user-selected relative humidity of the breathing gases as well as to deliver a prescribed amount of the medicine based on a concentration of the medicine in the water. In aspects, a concentration of the medicine may be adjusted based on the amount of water calculated to maintain the desired humidity. In other aspects, as detailed above, humidifier 300 may not include a controller and valve 316 may be controlled by the ventilator (e.g., ventilator 100). In the depicted aspect, controller 310 may command valve 316 using Pulse Width Modulation (PWM) or some other suitable driving method to provide "bursts" of water to the hollow cone atomizer 302. In these aspects, the duration and timing of bursts (as controlled by the opening and closing of the valve 316) provides a prescribed amount of high-pressure water to the hollow cone atomizer 302. These controlled bursts or pulses allow the hollow cone atomizer 302 to deliver a specific amount of atomized water (e.g., in a cone pattern of extremely small water droplets) to the gas stream, thereby preventing or reducing over or under humidification as well as delivering a prescribed amount of a dissolved medicine, if desired.

Additionally, the hollow cone atomizer 302 is configured to spray water (or water and medicine) in a hollow-cone pattern of extremely small water droplets at a low flow rate. The low flow rate further enables the hollow cone atomizer 302 to prevent or reduce over humidification. In some aspects, to achieve a desired humidity, the water flow rate is dependent on the gas flow rate. For instance, an average water flow rate as low as 0.04 ml/min may be delivered at a gas flow rate of 1 liters/min; whereas an average water flow rate as high as 9 ml/min may be delivered at a gas flow of 200 liters/min. The atomizer is designed to provide a minimum water flow rate of at least 9 ml/min so it can accommodate the maximum gas flow rate of 200 liters/min. Thus, to accommodate lower gas flow rates, the solenoid valve may be pulsed with shorter durations and/or longer intervals between pulses to deliver less water flow. In this case, the atomizer may deliver pulses of water at 30 ml/min timed and spaced to provide an average water flow rate of 1 ml/min. Even at a higher water flow rates, unlike other atomizers, a hollow cone atomizer may be utilized with shorter durations and longer intervals that are still short enough to provide consistent humidification.

In general, the hollow cone atomizer may be configured to deliver a water flow rate from 0.1 to 40.0 ml/min to breathing gases flowing by the hollow cone atomizer 302 in the flow path 304 exhibiting a gas flow rate from 1 to 200 liters/min. These water flow rates are exemplary only and not meant to be limiting. Other suitable water flow rates for use with the hollow cone atomizer are known by a person of skill in the art. In some aspects, the humidifier 300 also includes a water filter 313. The water filter 313 prevents small debris from entering the water pump 318, the valve 316, and/or the hollow cone atomizer 302 by filtering out any debris from the water supply. As illustrated, the water filter 313 is located upstream of the water pump 318, the valve 316, and the hollow cone atomizer 302. In other aspects, the water filter 313 may be located downstream of the water pump 318 and upstream of the valve 316 and the hollow cone atomizer 302.

As illustrated, the humidifier 300 also includes a temperature sensor and/or humidity sensor 307 located in flow path 304 upstream of the hollow cone atomizer 302. In other aspects, a temperature senor and/or a humidity sensor 307 may be located within the ventilator (e.g., associated with the inspiratory module 104) upstream of the hollow cone atomizer 302 but separate and distinct from the humidifier 300. In these aspects, the temperature sensor and/or a humidity sensor 307 is not part of the humidifier 300 but is part of the ventilator (e.g., ventilator 100). The temperature sensor and/or humidity sensor 307 may be communicatively coupled to humidifier 300 and may provide temperature and/or humidity measurements to controller 310, which may then command the heating tube 319 (and/or a heating circuit, not shown) to maintain a desired temperature and/or humidity of the breathing gases flowing through flow path 304. Alternatively, the temperature sensor and/or humidity sensor 307 may provide temperature and/or humidity measurements to controller 110 of ventilator 100 and ventilator 100 may then command heating tube 319 (and/or a heating circuit, not shown) to maintain a desired temperature and/or humidity of the breathing gases flowing through flow path 304.

As illustrated, the humidifier 300 also includes a heating tube 319. The heating tube 319 includes a thermally-conductive material 306, such as aluminum, silver, copper, or other suitable metal or alloy (which, in some cases may be thinly plated with nickel to prevent corrosion), which is surrounded by a heating element 308. The heating element 308 may generate thermal energy via any suitable means, e.g., electrical, chemical, or otherwise, and may deliver the thermal energy to the thermally-conductive material 306 via any suitable means (e.g., via an external sleeve or blanket, internal or external wiring, etc.). As illustrated in FIG. 3, the heating tube 319 is in fluid communication with an inspiratory limb (e.g., inspiratory limb 132) of the ventilation tubing system (e.g., ventilation tubing system 130) along flow path 304. As further illustrated in FIG. 3, the thermally-conductive material 306 is exposed in the flow path 304 and contacts the breathing gases or water in the flow path 304. The heating element 308 surrounds the thermally-conductive material 306 and is not in contact with breathing gases or water in the flow path 304. In aspects, the heating element 308 may heat quickly, e.g., in one minute or less, and may be controlled by humidifier 300 and/or ventilator 100 to rapidly achieve a desired temperature of the breathing gases within heating tube 319. As such, ventilator 100 and/or humidifier 300 require very little start up time for humidifying the breathing gas.

The heating tube 319 is positioned directly downstream of the hollow cone atomizer 302, such that water sprayed from the hollow cone atomizer contacts the thermally-conductive material 306 of the heating tube 319. When the thin, hollow cone 323 of small droplets of water from the hollow cone atomizer 302 contacts the heated metal surface of the thermally-conductive material 306, the small droplets of water are immediately vaporized, turning into gaseous water vapor. This gaseous water vapor enters the stream of breathing gases 325 in flow path 304, forming a gaseous solution of humidified breathing gases 330. In some aspects, the temperature of the heating tube 319 is maintained using closed-loop control by controller 310 (or controller 110 of ventilator 100) to a level whereby the droplets emitted from the hollow cone atomizer 302 are vaporized, and a temperature of the humidified breathing gases 330 is regulated to maintain the water vapor in the breathing gases delivered to the patient at a user-selected humidity. For instance, in embodiments without a heated circuit, for a patient set point of 37 degrees C., the humidified breathing gases leaving the humidifier may be about 45 degrees C. to account for cooling in the inspiratory limb of the patient circuit. In other aspects, the temperature of the heating tube 319 is significantly hotter than needed for vaporization in order to raise the temperature of the humidified breathing gases 330 to a desired temperature sufficient to maintain the water vapor in the breathing gases at the user-selected humidity when cooling occurs in the ventilation tubing system. In aspects, the heating tube 319 may have a length from 2 inches to 7 inches. In some aspects the heating tube 319 has a length of 2 inches, 3 inches, or 4 inches.

Figure 4:
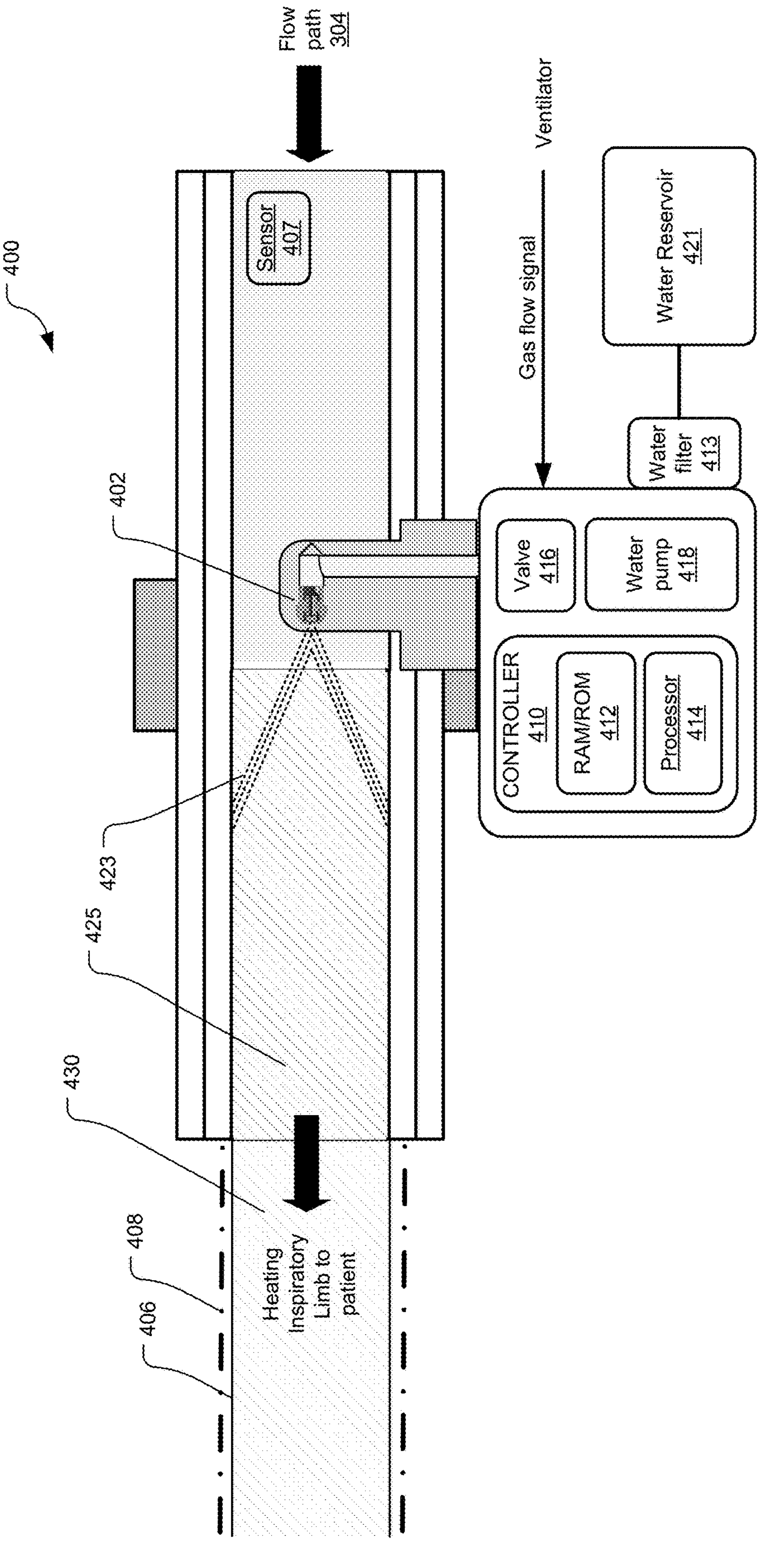
FIG. 4 is a partial, cross-sectional schematic diagram illustrating a second aspect of a humidifier including a hollow cone atomizer in a flow path of a ventilator during ventilation of a patient, in accordance with aspects of the disclosure.

FIG. 4 is a partial cross-sectional schematic diagram illustrating a second aspect of a humidifier 400 (similar to humidifier 218, detailed above) including a hollow cone atomizer 402 in a flow path 404 of a ventilator (similar to ventilator 200, detailed above) during ventilation of a patient 150, in accordance with aspects of the disclosure. As illustrated, humidifier 400 does not comprise a gas flow sensor and is integrated with the ventilator (e.g., ventilator 200). Unlike humidifier 300, humidifier 400 does not comprise a heating tube but delivers humidified breathing gases 430 to a heating inspiratory limb 406 (similar to heating inspiratory limb 232). However, in aspects, as detailed above, humidifier 400 may also be configured with a heating tube (such as heating tube 319) and be implemented with a heating inspiratory limb 406 and a heated exhalation limb (such as heated exhalation limb 234). In aspects, the hollow cone atomizer 402 may be a pressure swirl atomizer. As illustrated, the hollow cone atomizer 402 is positioned to spray water (or water and medicine) directly into the flow path 404 of the breathing gases. As humidifier 400 is integrated with the ventilator, the flow path 404 is within the pressure generating system 102 of ventilator 200. However, where the humidifier is a stand-alone device, the flow path is downstream from the pressure generating system 102 but upstream from the heating circuit 230, as illustrated in FIG. 2.

In some aspects, the humidifier 400 also includes a water reservoir 421, a high-pressure water pump 418 and a valve 416, which are in fluid communication with the hollow cone atomizer 402. For example, the water pump 416 pumps water from the water reservoir 421 towards the hollow cone atomizer 402 through valve 416. In some aspects, the valve 416 is a fast-response solenoid valve that delivers high-pressure water to the hollow cone atomizer 402. In some cases, the water may comprise a dissolved medicine at a known concentration.

As illustrated, humidifier 400 further includes a controller 410 including memory 412 and at least one processor 414. Controller 410 may be operative to receive an inspiratory flow command from the ventilator (e.g., ventilator 200) and may command valve 416 to deliver an amount of water sufficient to maintain a user-selected relative humidity of the breathing gases. In other aspects, as detailed above, humidifier 400 may not include a controller and valve 416 may be controlled by the ventilator (e.g., ventilator 200). In the depicted aspect, controller 410 may command valve 416 using Pulse Width Modulation to provide “bursts” of water to the hollow cone atomizer 402. In these aspects, the duration and timing of bursts (as controlled by the opening and closing of the valve 416) provides a prescribed amount of high-pressure water to the hollow cone atomizer 402. These controlled bursts or pulses allow the hollow cone atomizer 402 to deliver a specific amount of atomized water (e.g., in a cone pattern of extremely small water droplets) to the gas stream, thereby preventing or reducing over or under humidification.

As with humidifier 300, humidifier 400 may include a second atomizer (not shown) in flow path 404. In this case, the second atomizer may be designed based on the fluid characteristics of a medicine or medicines to be delivered. For instance, when medicines are not water-soluble, these medicines may be significantly more viscous than water, and therefore the dimensions of the atomizer may need to be adjusted to appropriately atomize the medicine. Depending on the fluid characteristics, this second atomizer may be a more conventional (non-pressure swirl) atomizer type. The second atomizer may use the same type of reservoir, pumping and valve system, as described below. Alternatively, depending on the fluid characteristics of the medicine, the second atomizer may require adjustments to the reservoir, pumping, and/or valve system as appropriate for the fluids and the pressures used. In aspects, a medicine dissolved in a biologically-compatible solvent is delivered to the second atomizer via a suitable valve and/or pumping system. Similar to the first atomizer, the second atomizer disperses the medicine-solvent solution in small droplets into the flow path. Depending on the location of the second atomizer and the fluid characteristics of the medicine-solvent solution, the small droplets may or may not be vaporized by the humidifier 400. However, it is contemplated that small droplets of the medicine-solvent may deliver a prescribed amount of the medicine to the breathing gases without requiring vaporization. While the second atomizer could be located before or after the first atomizer (e.g., atomizer 402), the preferred location is downstream of the first atomizer. In some cases, the second atomizer may be a removable plug-in device, e.g., connected via an access port in the humidifier housing that may be covered when not in use.

As with hollow cone atomizer 302, the hollow cone atomizer 402 is configured to spray water (or water and medicine) in a hollow-cone pattern of extremely small water droplets at a low flow rate. The low flow rate further enables the hollow cone atomizer 402 to prevent or reduce over humidification. As detailed above, the hollow cone atomizer may be configured to deliver a water flow rate from 0.1 to 40.0 ml/min to breathing gases flowing by the hollow cone atomizer 402 in the flow path 404 exhibiting a gas flow rate from 1 to 200 liters/min. These water flow rates are exemplary only and not meant to be limiting. Other suitable water flow rates for use with the hollow cone atomizer 402 are known by a person of skill in the art. In some aspects, the humidifier 400 also includes a water filter 413. The water filter 413 prevents small debris from entering the water pump 418, the valve 416, and/or the hollow cone atomizer 402 by filtering out any debris from the water supply. As illustrated, the water filter 413 is located upstream of the water pump 418, the valve 416, and the hollow cone atomizer 402. In other aspects, the water filter 413 may be located downstream of the water pump 418 and upstream of the valve 416 and the hollow cone atomizer 402.

As illustrated, the humidifier 400 also includes a temperature sensor and/or humidity sensor 407 located in flow path 404 upstream of the hollow cone atomizer 402. In other aspects, a temperature senor and/or a humidity sensor 407 may be located within the ventilator (e.g., associated with the inspiratory module 104) upstream of the hollow cone atomizer 402 but separate and distinct from the humidifier 400. In these aspects, the temperature sensor and/or a humidity sensor 407 is not part of the humidifier 400 but is part of the ventilator (e.g., ventilator 200). The temperature sensor and/or humidity sensor 307 may be communicatively coupled to humidifier 400 and may provide temperature and/or humidity measurements to controller 410, which may then command the heating element 408 (or the heating tube, not shown) to maintain a desired temperature and/or humidity of the breathing gases flowing through flow path 404. Alternatively, the temperature sensor and/or humidity sensor 407 may provide temperature and/or humidity measurements to controller 110 of ventilator 200 and ventilator 200 may then command heating element 408 (or the heating tube, not shown) to maintain a desired temperature and/or humidity of the breathing gases flowing through flow path 404.

Unlike humidifier 300, the humidifier 400 does not include a heating tube. However, humidifier 400 is in fluid communication with a heating inspiratory limb 406 (similar to heating inspiratory limb 232). Unlike heating tube 319, which is in contact with a minimal portion of a patient circuit, a heating circuit (similar to heating circuit 230) may comprise a heating element 408 (depicted by dashed lines) that is in contact with a substantial portion of the patient circuit, including heating inspiratory limb 406 and/or a heating exhalation limb (not shown). The heating element 408 may be independent and may surround (e.g., as a heater blanket or heater sleeve) a traditional, disposable patient circuit to form the heating inspiratory limb 406. In this case, the heating element 408 may be non-disposable and capable of sterilization between patients; or the heating element may itself be disposable. Alternatively, the heating element 408 may be integrated (e.g., wired) on the exterior or the interior of a custom, disposable patient circuit to form the heating inspiratory limb 406. The heating element 408 may generate thermal energy via any suitable means, e.g., electrical, chemical, or otherwise, and may deliver the thermal energy to heat the patient circuit via any suitable means (e.g., via an external sleeve or blanket, internal or external wiring, etc.). In aspects, the heating element 408 may heat quickly, e.g., in a minute or less, and may be controlled by humidifier 400, a probe (such as probe 236), and/or ventilator 200 to achieve a desired temperature. As illustrated, heating inspiratory limb 406 is in substantial fluid communication with humidified breathing gases 430 to regulate humidity and prevent rainout in heating inspiratory limb 406. In some cases, a heating circuit may comprise heating inspiratory limb 406 without a heating exhalation limb. In this case, heating inspiratory limb 406 may regulate temperature of the humidified breathing gases 430 and may prevent rainout in the heating inspiratory limb 406 as well as minimizing rainout the non-heated exhalation limb (not shown).

As illustrated, the heating inspiratory limb 406 is positioned directly downstream of the humidifier 400, such that atomized water from the hollow cone atomizer 402 contacts the heating inspiratory limb 406. For example, when the hollow cone 423 of small droplets of water from the hollow cone atomizer 402 contact the heated surface of the heating inspiratory limb 406, the small droplets of water are vaporized, turning into gaseous water vapor. This gaseous water vapor enters the stream of breathing gases 425 in flow path 404, forming a gaseous solution of humidified breathing gases 430. Alternatively, as discussed above, humidifier 400 may further comprise a heating tube (not shown). In this case, humidified breathing gases leaving the humidifier 400 enter the heating inspiratory limb 406, which is modulated to control the temperature of the breathing gases at the patient wye fitting 170. In some aspects, the heating inspiratory limb 406 is controlled such that a temperature gradient exists whereby the temperature at the entrance of the heating inspiratory limb 406 is higher than at the exit (wye fitting 170) due to the heating tube (e.g., heating tube 319) upstream of the heating inspiratory limb 406. In other aspects, humidifier 400 does not include a heating tube (as shown) and the heating and water vaporization are achieved using the heating inspiratory limb 406 alone. In some aspects, the temperature of the heating inspiratory limb 406 is maintained using closed-loop control by controller 410 (or controller 110 of ventilator 200) to a level whereby the droplets emitted from the hollow cone atomizer 402 are vaporized, and a temperature of the humidified breathing gases 430 within the heating inspiratory limb 406 may be regulated to maintain an amount of water vapor in the breathing gases delivered to the patient at a user-selected humidity. In some cases, as described with respect to FIG. 2, feedback from a probe (such as probe 236) may provide temperature and/or humidity measurements of the humidified breathing gases 430 at the wye fitting 170 to the controller 410 (or the controller 110). In this way, the heating element 408 may be adjusted to increase or decrease a temperature of the heating inspiratory limb 406 in order to maintain the user-selected humidity of the breathing gases at the wye fitting 170.

Figure 5:
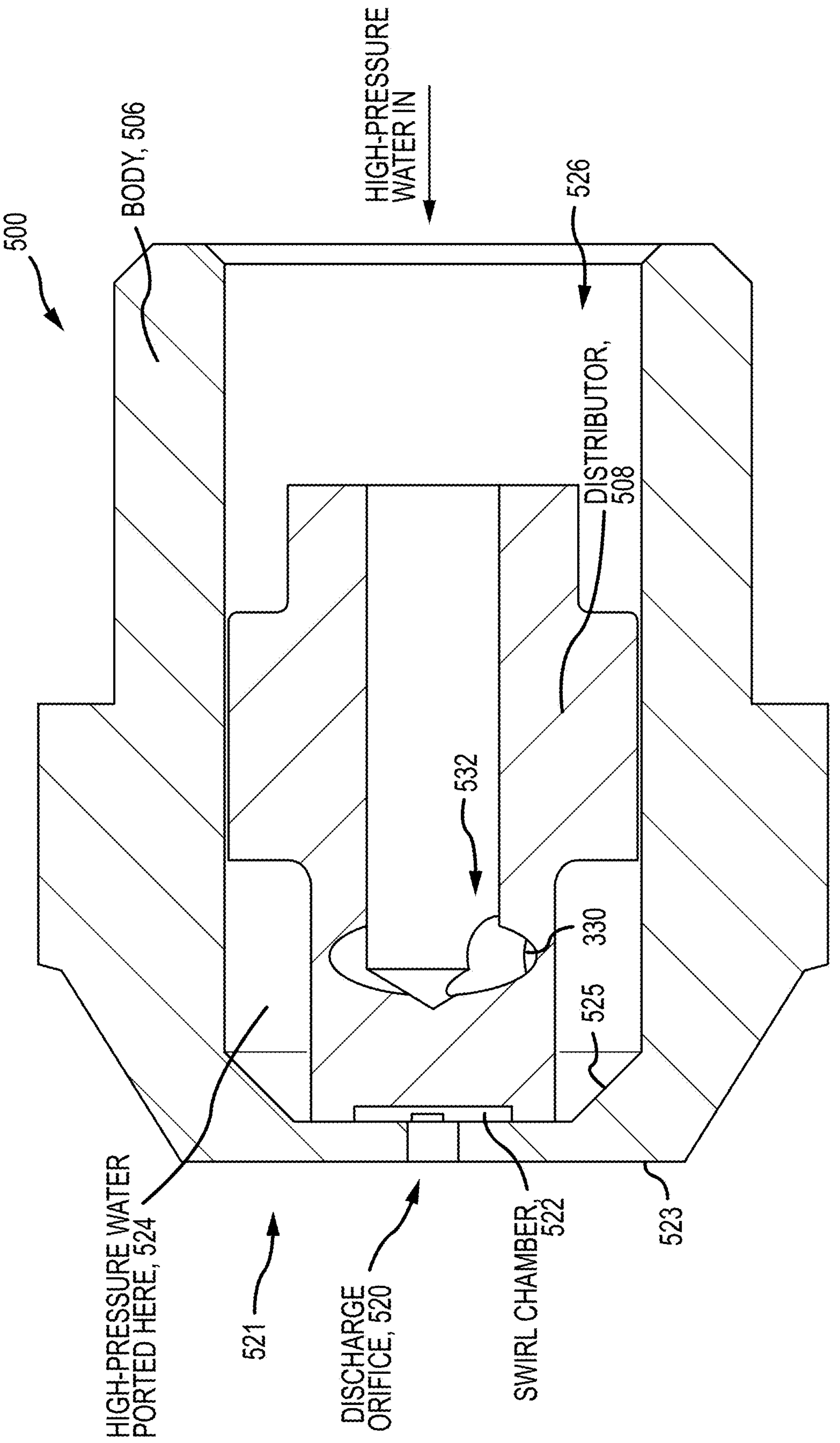
FIG. 5 is a partial, cross-sectional schematic diagram illustrating a spray body and a distributor of a type of hollow cone atomizer referred to as a pressure swirl atomizer, in accordance with aspects of the disclosure.
Figure 6:
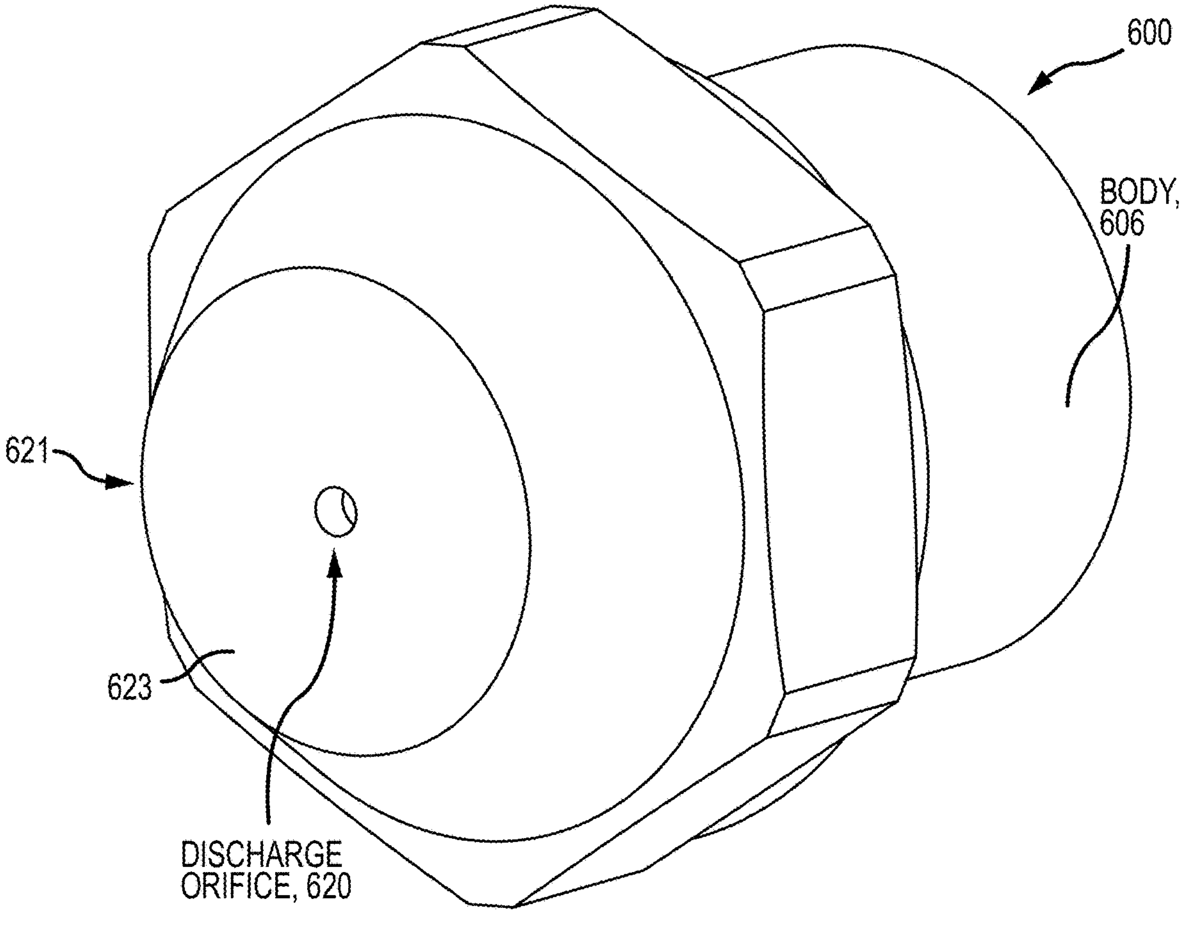
FIG. 6 is an isometric view of a schematic diagram illustrating a spray body of a type of hollow cone atomizer referred to as a pressure swirl atomizer, in accordance with aspects of the disclosure.
Figure 7:
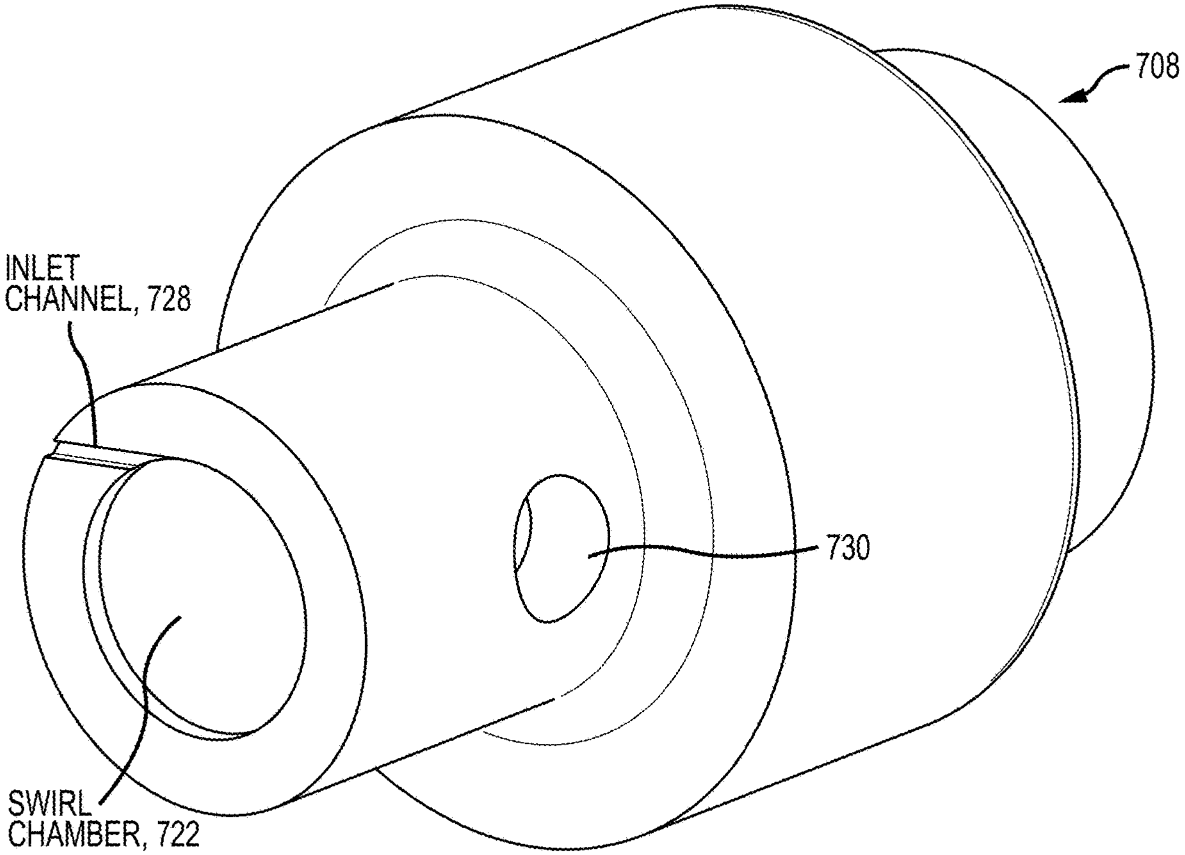
FIG. 7 is an isometric view of a schematic diagram illustrating a distributor of a type of hollow cone atomizer referred to as a pressure swirl atomizer, in accordance with aspects of the disclosure.

FIG. 5 is a partial cross-sectional schematic diagram illustrating a spray body 506 and a distributor 508 of a type of hollow cone atomizer referred to as a pressure swirl atomizer 500, in accordance with aspects of the disclosure. A pressure swirl atomizer is a type of hollow cone atomizer that delivers high performance atomization at low liquid flow rates. FIG. 6 is an isometric view of a schematic diagram illustrating a spray body 606 of a type of hollow cone atomizer referred to as a pressure swirl atomizer 600, in accordance with aspects of the disclosure. FIG. 7 is an isometric view of a schematic diagram illustrating a distributor 708 of a type of hollow cone atomizer referred to as a pressure swirl atomizer 700, in accordance with aspects of the disclosure.

As illustrated in FIGS. 5 and 6, a discharge orifice 520 (or 620) on the spray body 506 (or 606) extends through a first end 521 (or 621) of the spray body 506 (or 606) and connects to an interior passageway 526 within the spray body 506 (not shown in FIG. 6). The first end 521 (or 621) has an exterior wall 523 (or 623) and an interior wall 525.

As illustrated in FIG. 5, the distributor 508 is received within the interior passageway 526 of the spray body 506 and mechanically biased against the interior wall 525 of the first end 521 of the spray body 506. In some aspects, the distributor 508 is mechanically biased with a resilient material, such as a spring. In further aspects, a swirl chamber 522 of the distributor 508 abuts and is in fluid communication with the discharge orifice 520.

As illustrated by FIG. 7, a single inlet channel 728 in the distributor 708 provides a passageway or opening for water to flow from an interior passageway (e.g., interior passageway 526 of FIG. 5) to the swirl chamber 722 (or 522). In some aspects, the water flows through the internal passageway 526, a distributor passage 532, one or more passage apertures 530 (or 730), and/or a high pressure water port 524 to reach the inlet channel 728.

When high pressure water (or water and medicine) (generally greater than 50 psi, such as 300 psi) enters the spray body 506 (or 606) of the pressure swirl atomizer 500 (or 600), the water is ported to a single inlet channel 728 (as illustrated in FIG. 7). Although some hollow cone atomizers may include more than one inlet channel (not shown), practical applications for such hollow cone atomizers generally utilize higher water flow rates. For instance, traditional pressure swirl atomizers include multiple inlet channels and are used to inject water upstream of a turbine of a high performance jet engine to provide a temporary boost in thrust (because the water increases gas density across the turbine). In this case, high water flows can be delivered due to the high gas flows across the turbine. In the present application, to achieve low water flow rates suitable for the low gas flow rates utilized to ventilate a patient, it has been discovered that a pressure swirl atomizer designed with a single inlet channel enables precise delivery of highly atomized water at very low water flow rates. However, to the extent that adjusting the duration and/or interval of pulses delivered to a hollow cone atomizer having more than one inlet channel can produce low water flow rates suitable for the present application, such a hollow cone atomizer can be implemented by the methods and systems herein to humidify breathing gases.

The water may be pumped into the pressure swirl atomizer (e.g., 500 or 600) at any suitable pressure, such as from 50 psi to 1500 psi. The lower the pressure utilized, however, the slower the water flow rate that exits the pressures swirl atomizer. The inlet channel 728 directs the high-pressure water tangentially into the swirl chamber 522 (or 722), resulting in a high velocity rotating fluid field in the swirl chamber 522 (or 722). The dimensions of the inlet channel 728 and discharge orifice 520 (or 620) are minute. For example, the total inlet area of the inlet channel 728 may be 0.005 to 0.3 $mm^2$. In some aspects, the total inlet area of the inlet channel 728 is 0.008 $mm^2$ or 0.007 $mm^2$, 0.006 $mm^2$, 0.16 $mm^2$, or 0.18 $mm^2$. In other examples, the diameter of the discharge orifice 520 (or 620) is from 0.4 to 2.0 mm. In some aspects, the diameter of the discharge orifice 520 (or 620) is 0.4 mm, 0.5 mm, 0.6 mm, 0.7, 0.8 mm, 0.9 mm, or 1.0 mm. The dimensions of the discharge orifice length/diameter ratio and swirl chamber diameter are also very small. For example, the discharge orifice length/diameter ratio may be from 0.5 to 4.0. In some aspects, the discharge orifice length/diameter ratio may be 0.4, 0.5, 0.6, 0.7, 0.8, 0.9, 1.0, 1.1, 1.2, 1.3, or 1.4. For example, the swirl chamber diameter may be from 1.0 to 4.0 mm. In some aspects, the swirl chamber diameter may be 1.5 mm, 1.4 mm, 1.3 mm, 1.6 mm, 1.7 mm, or 1.8 mm. These dimensions are exemplary only and are not meant to be limiting. Any suitable dimensions for providing a hollow cone spray with a thin wall of small water droplets may be utilized as would be understood by a person of skill in the art.

Because this rotating field is at high pressure relative to ambient, a vortex is created, causing the rapidly spinning water to be expelled out of the discharge orifice 520 (or 620) with high rotational velocity. The result is a "hollow cone" (e.g. 323 or 423) of very small water droplets. In some aspects the Sauter Mean Diameter (water droplet size) is from 1-100 microns. For example, the water droplet size may be 4, 5, or 6 microns. In further aspects, a cone wall thickness of the water droplet stream is from 0.01 to 0.8 mm. For example, the cone wall thickness may be in a range of 0.04 to 0.07 mm. In additional aspects, a cone angle (the interior spread of the cone, shown in FIGS. 3 and 4) is greater than 30 degrees. For example, the cone angle may be from 80 degrees to 130 degrees. In some aspects, the pressure swirl atomizer 500 (or 600) can produce cone angles of greater than 90 degrees, a cone wall or film thickness of less than 0.1 mm, and/or droplet sizes of less than 10 microns. These characteristics of a high angle, very thin hollow cone 323 (or 423) of very small water droplets differentiate a pressure swirl atomizer from other types of atomizers.

Figure 8:
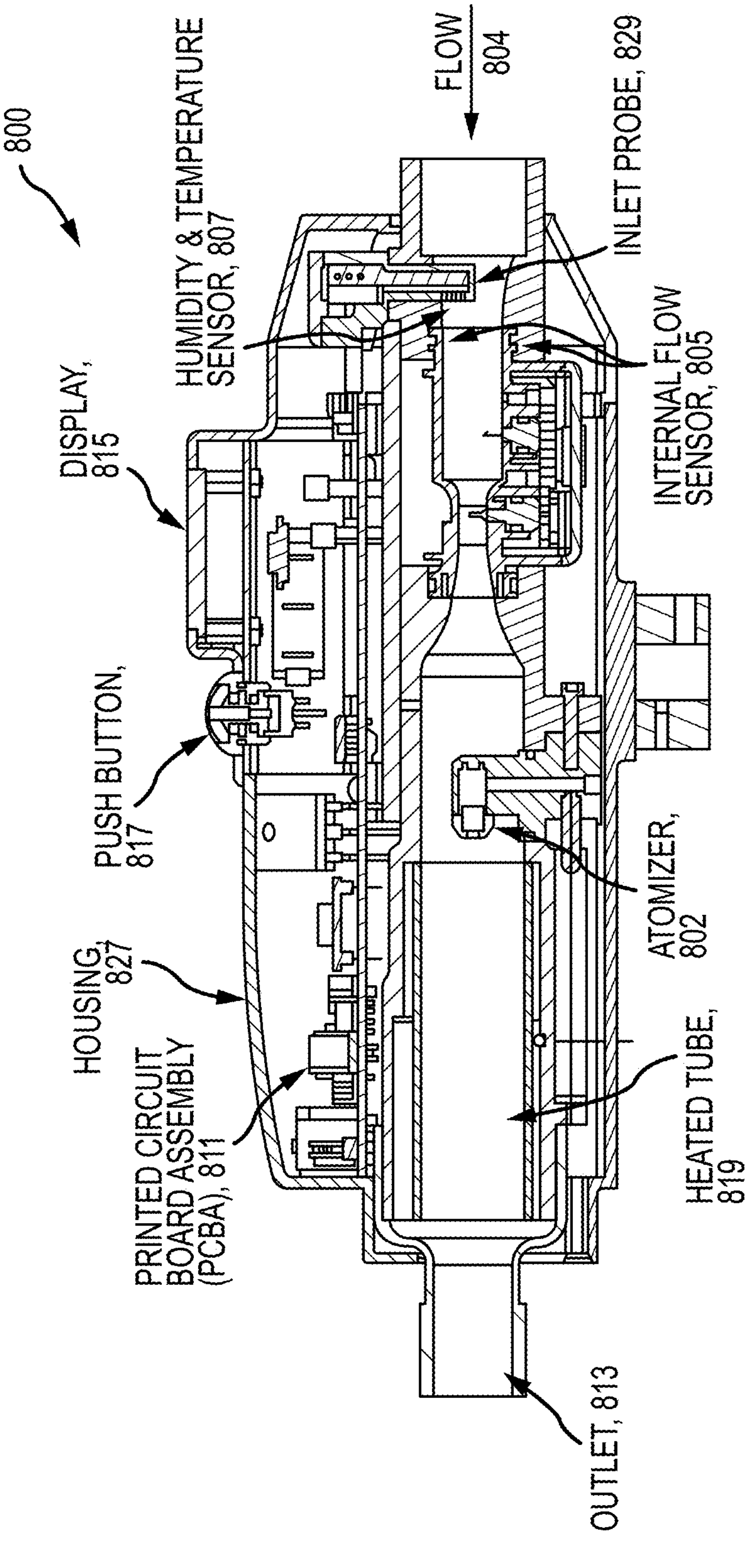
FIG. 8 is a partial, cross-sectional schematic diagram illustrating a stand-alone humidifier including a hollow cone atomizer and a gas flow sensor, in accordance with aspects of the disclosure.

FIG. 8 is a partial, cross-sectional schematic diagram illustrating a stand-alone humidifier 800 including a hollow cone atomizer 802 and a gas flow sensor 805, in accordance with aspects of the disclosure. Humidifier 800 includes a heating tube 819 and is similar to humidifier 300 in many respects. However, humidifier 300 does not include a gas flow sensor and is integrated into a ventilator, whereas humidifier 800 includes an internal gas flow sensor 805 and is a stand-alone device. Humidifier 800 is also similar to humidifier 118, which is a stand-alone humidifier installed outside of ventilator 100 near the inspiratory port 125.

As illustrated, humidifier 800 is within a housing 827 and includes hollow cone atomizer 802 in a flow path 804 of a ventilator (similar to ventilator 100 or ventilator 200, detailed above) during ventilation of a patient 150, in accordance with aspects of the disclosure. Housing 827 may be constructed of any suitable material for encasing the components and circuitry of the humidifier 800, which is further suitable for sterilization between patients. As with humidifier 118, humidifier 800 comprises a heating tube 819 (similar to heating tube 119 and 319). While humidifier 800 is not shown in fluid communication with a heating inspiratory limb (e.g., such as heating inspiratory limb 232), this configuration is contemplated and humidifier 800 may easily be implemented in such a system. In aspects, the hollow cone atomizer 802 may be a pressure swirl atomizer. As illustrated, the hollow cone atomizer 802 is positioned to spray water directly into the flow path 804 of breathing gases. As humidifier 800 is a stand-alone device, the flow path 804 is downstream from the pressure generating system 102 but upstream from the ventilator tubing system 130, as illustrated in FIGS. 1 and 2.

As illustrated, humidifier 800 further includes computer circuitry 811, which includes a controller (such as controller 310 or controller 410), memory (such as memory 312 or memory 412), and at least one processor (such as processor 314 or processor 414). As detailed above, the controller of humidifier 800 may command a valve (not shown) to provide "bursts" of water (or water and medicine) to the hollow cone atomizer 802. The duration and timing of bursts (as controlled by the opening and closing of the valve) provides a prescribed amount of high-pressure water to the hollow cone atomizer 802. These controlled bursts or pulses allow the hollow cone atomizer 802 to deliver a specific amount of atomized water (e.g., in a cone pattern of extremely small water droplets) to the gas stream, thereby preventing or reducing over or under humidification.

As illustrated, the humidifier 800 also includes a temperature sensor and/or humidity sensor 807 located in flow path 804 upstream of the hollow cone atomizer 802. Humidifier 800 may also include a probe inlet 829 for receiving temperature and/or humidity measurements at the wye fitting from a probe (such as probe 236). The temperature sensor and/or humidity sensor 807 (and/or probe inlet 829) may be communicatively coupled to humidifier 800 and may provide temperature and/or humidity measurements to the controller, which may then command the heating tube 819 (and/or the heating circuit, not shown) to maintain a desired temperature and/or humidity of the breathing gases flowing through flow path 804. Humidifier 800 further includes an internal gas flow sensor 805, enabling the humidifier 800 to be a stand-alone device. As illustrated, internal gas flow sensor 805 may be downstream of temperature sensor and/or humidity sensor 807, and upstream of the hollow cone atomizer 802. The internal gas flow sensor 805 may provide a gas flow signal to the controller for determining a desired amount of water to be delivered to the gas stream in flow path 804.

As illustrated, the humidifier 800 also includes a heating tube 819, which is similar to heating tube 119 and 319 described above. The heating tube 819 includes a thermally-conductive material that is surrounded by or integrated with a heating element (not shown). As described above, a heating element may generate thermal energy via any suitable means, e.g., electrical, chemical, or otherwise, and may deliver the thermal energy to the thermally-conductive material via any suitable means (e.g., via an external sleeve or blanket, internal or external wiring, etc.). As illustrated in FIG. 8, the heating tube 819 is in fluid communication with outlet 813, which is in fluid communication with a heating or non-heating inspiratory limb of the ventilation tubing system (not shown). As described above, the heating tube 819 is positioned directly downstream of the hollow cone atomizer 802, such that when a hollow cone of small droplets of water (or water and medicine) from the hollow cone atomizer 802 contacts the heated surface of the heating tube 819, the small droplets of water are vaporized, turning into gaseous water vapor. This gaseous water vapor enters the stream of breathing gases in flow path 804, forming a gaseous solution of humidified breathing gases.

The humidifier 800 further includes a display 815 and a push button 817. Display 815 may provide, for example, a user-selected humidity set point (e.g., between 50% and 99%), a user-selected temperature of humidified breathing gases (e.g., within a range of 32 to 42 degrees C.), a measured humidity of breathing gases (e.g., as measured at the wye fitting by a probe, or at another suitable location), a measured temperature of humidified breathing gases (e.g., as measured at the wye fitting by a probe, or at another suitable location), and alarms and/or alerts. Push button 817, which may alternatively be represented by one or more controls of a touch-enabled graphical user interface (GUI) provided by display 815, enables selection of a humidity set point (e.g., between 50% and 99%), selection of a temperature for humidified breathing gases (e.g., within a range of 32 to 42 degrees C.), and selection of alarm and/or alert thresholds.

Figure 9:
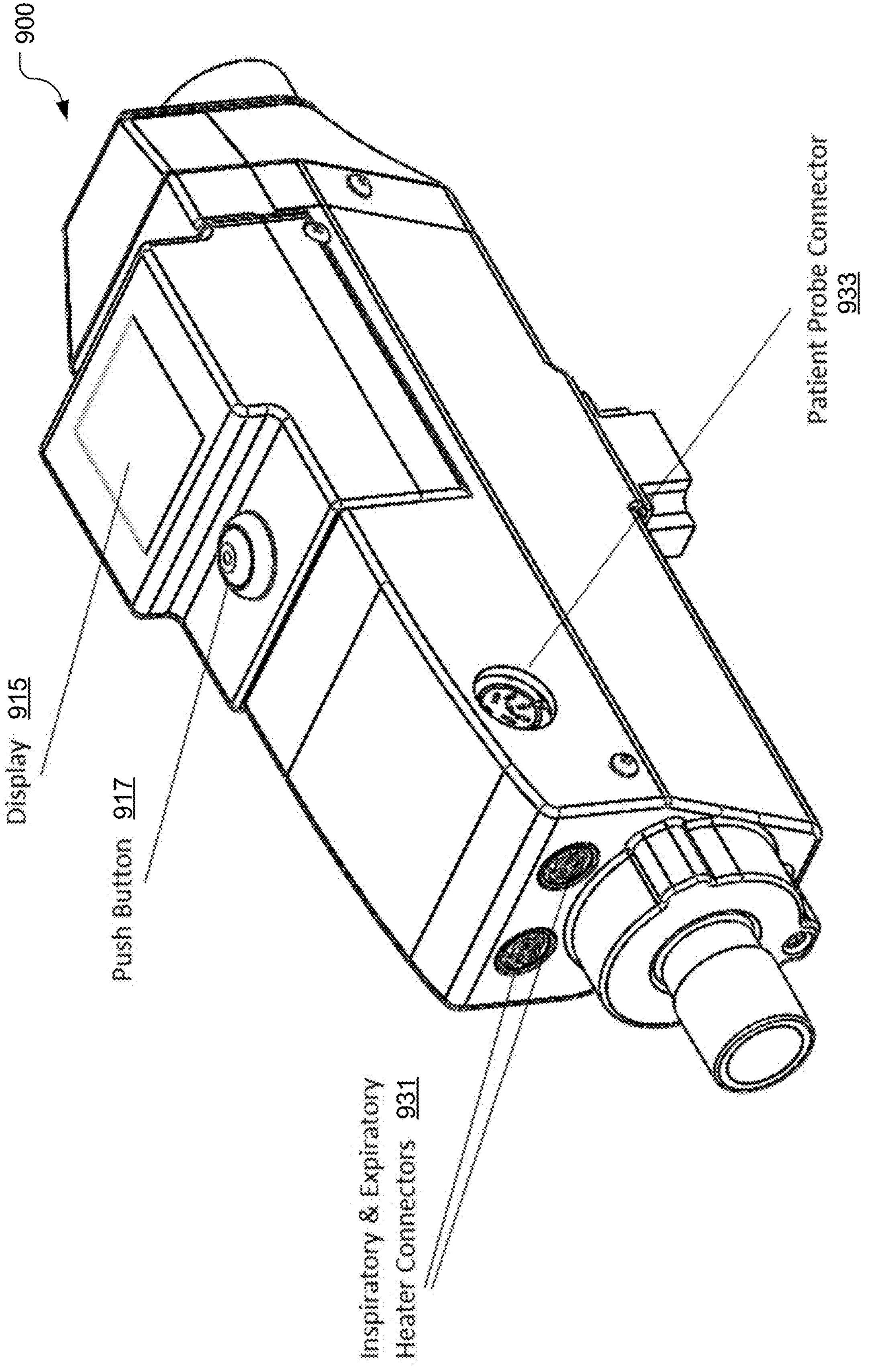
FIG. 9 is an isometric view of a schematic diagram illustrating a stand-alone humidifier within a housing, in accordance with aspects of the disclosure.

FIG. 9 is an isometric view of a schematic diagram illustrating a stand-alone humidifier 900 within a housing (such as housing 827, describe above), in accordance with aspects of the disclosure. Humidifier 900 is similar to humidifier 800, as described above. As illustrated, humidifier 900 includes a display 915 (such as display 815, described above), a push button 917 (such as push button 817, described above), and a patient probe connector 933 (e.g., in communication with probe inlet 829, described above). Humidifier 900 further includes inspiratory and expiratory heater connections 931 for powering and/or controlling heating elements associated with regulating a temperature of a heating inspiratory limb (e.g., heating inspiratory limb 232) and/or a heating exhalation limb (e.g., heating exhalation limb 234).

FIGS. 10A-10D illustrate alternative spray patterns of hollow cone or full cone atomizers, in accordance with aspects of the disclosure.

Figure 10A:
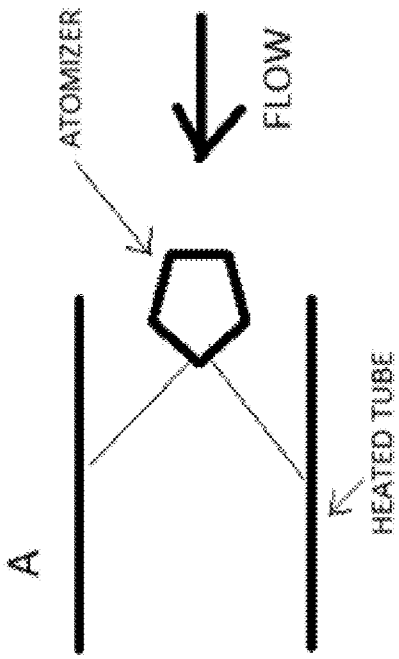
FIGS. 10A-10D illustrate alternative spray patterns of hollow cone or full cone atomizers, in accordance with aspects of the disclosure.

FIG. 10A illustrates a spray pattern of a hollow cone atomizer with an axially-directed spray of small water droplets impinging on an inside diameter of a heated tube. In this case, a direction of the spray is in the same direction as gas flow. Here, because the trajectory of the water droplets does not oppose the momentum of the incoming gas flow, the effect of the gas flow causes minimal disturbance to the path of the water droplets towards their target (i.e., the heated tube). In aspects, a full cone atomizer may also be used, but is less desirable because further heating downstream of the atomizer may be required to fully evaporate the injected water. Additionally, it may be difficult to deliver a low water flow with full cone atomizer.

Figure 10B:
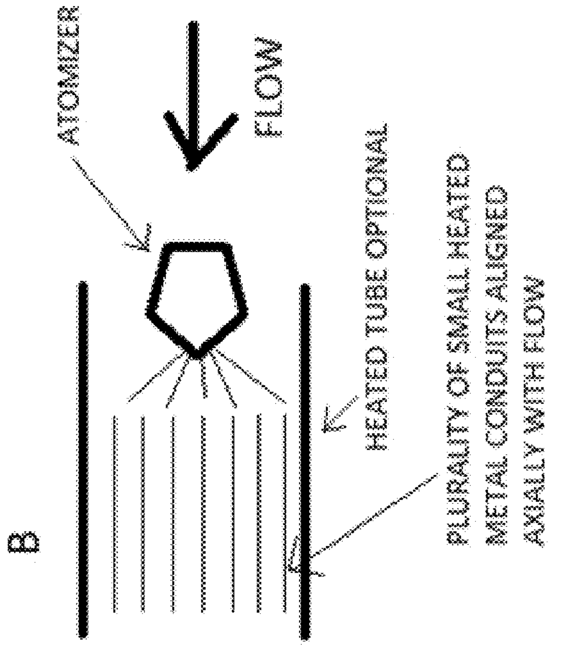

FIG. 10B illustrates a spray pattern of a hollow cone or full cone atomizer with an axially-directed spray impinging on a plurality of small heated metal conduits that are aligned axially with the gas flow. These conduits are formed of a thermally-conductive material, such as an aluminum honeycomb or similar metal or alloy. In aspects, a heated tube may be used in conjunction with the heated conduits. However, in this case, heating the conduits may not be controlled as precisely as a heating tube, causing vaporization effectiveness to be less certain. Furthermore, cleaning of the conduits may be more difficult than a heating tube. If a full cone atomizer is used, it may be difficult to deliver a low water flow.

Figure 10D:
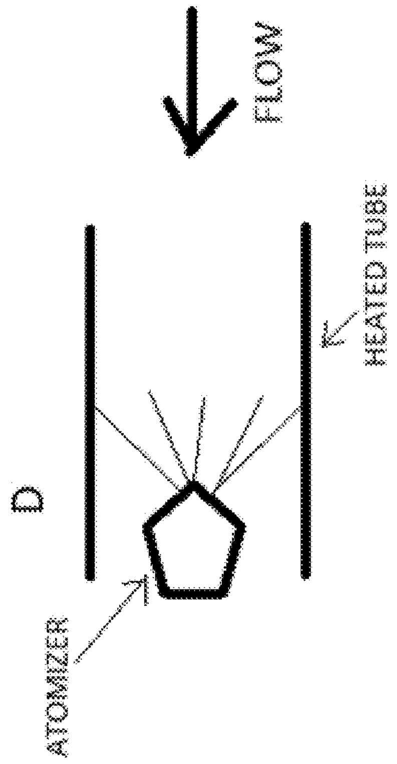
Figure 10C:
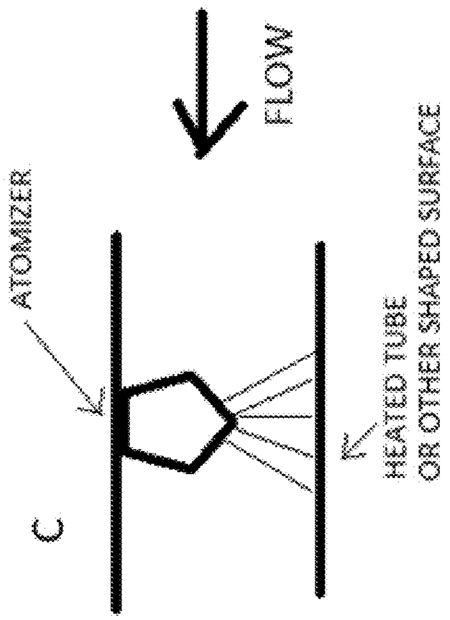

FIG. 10C illustrates a spray pattern of a hollow cone or full cone atomizer with a perpendicularly-directed spray impinging on a portion of the inside diameter of a heating tube. Alternatively, the perpendicularly-directed spray may impinge on an alternatively-shaped heated surface, with or without an additional heating tube. In this example, vaporization effectiveness may be less certain and/or may require a higher temperature due to the lower heated surface area. If a full cone atomizer is used, it may be difficult to deliver a low water flow.

FIG. 10D illustrates a spray pattern of a hollow cone or full cone atomizer with an axially-directed spray impinging on an inside diameter of a heating tube. In this case, the spray is directed opposite (facing) a direction of the gas flow. In this case, by injecting into the face of the gas stream, more water droplets may be swept into the center of the gas flow stream and would not contact the heated tube surface. Here, vaporization effectiveness may be less certain and further heating may be required downstream of the humidifier to ensure full vaporization. If a full cone atomizer is used, it may be difficult to deliver a low water flow. Additional descriptions and interactions between the components shown in FIGS. 1-10D are provided in method 1100, as described below and/or as illustrated in FIGS. 1-10D.

Figure 11:
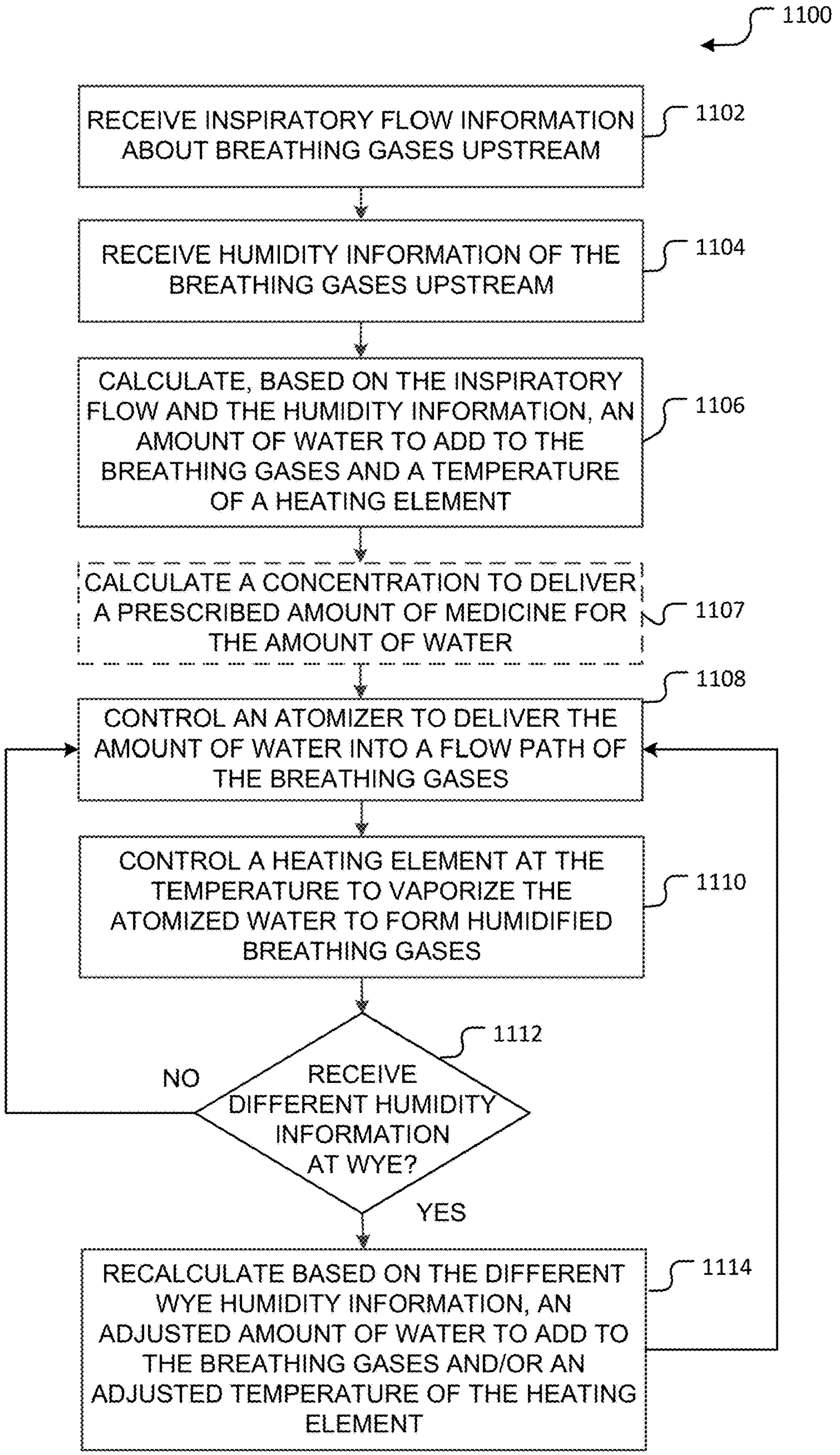
FIG. 11 is a flow diagram illustrating a method for humidifying ventilator delivered breathing gas, in accordance with aspects of the disclosure.

FIG. 11 is a flow diagram illustrating a method 1100 for humidifying breathing gases for delivery by a ventilator to a patient, in accordance with aspects of the disclosure. Method 1100 reduces and/or prevents over or under humidification of breathing gases, where over humidification causes rainout in the patient circuit and under humidification causes patient airway dryness, airway injury, and/or discomfort. For example, method 1100 reduces and/or prevents over or under humidification by utilizing a hollow cone atomizer (e.g., a pressure swirl atomizer) to deliver a controlled amount of water to the breathing gases and/or by controlling a temperature of a heating element within a heating tube of the humidifier (and/or within a heating circuit) to maintain a desired humidity of the breathing gases. In addition to preventing or reducing over or under humidification, method 1100 can utilize less water resulting in less exhalation filter saturation. Further, because method 1100 utilizes a heating element adapted to quickly reach a desired temperature (e.g., in one minute or less), method 1100 requires minimal warm up time. In some aspects, the use of a heating element to heat the expiratory inspiratory limb by method 1100 can further prevent rainout in the exhalation limb. In some aspects, method 1100 is performed by a humidifier integrated with a ventilator. In other aspects, method 1100 is performed by a stand-alone humidifier coupled to a ventilator.

As illustrated, method 1100 begins with receive operation 1102. At receive operation 1102, the humidifier receives inspiratory flow information about breathing gases upstream from an atomizer of the humidifier from a ventilator and/or one or more flow sensors. In some aspects, the one or more flow sensors are part of the humidifier. In other aspects, the one or more flow sensors are part of the ventilator. The inspiratory flow information may be a ventilator inspiratory flow command or a measured inspiratory flow rate.

At receive operation 1104, the humidifier receives humidity information from at least one of the ventilator or one or more upstream humidity sensors. The humidity information may be relative humidity and/or a temperature of the breathing gases upstream of the atomizer of the humidifier. For example, the breathing gases may be in a flow path of a pressure generating system of a ventilator.

At calculate operation 1106, a processor of the humidifier calculates an amount of water to add to the breathing gases to reach a desired humidity based on the inspiratory flow information and/or the humidity information. In some aspects, the desired humidity may be a user-selected humidity set point (e.g., as a humidity percentage) between 50% and 99%. This range is exemplary only and is not meant to be limiting. Any desired humidity that is greater than the relative humidity of the upstream breathing gases may be utilized. The humidifier during calculate operation 1106 may utilize the inspiratory flow information and/or the humidity information (which humidity information may include a relative humidity as well as a temperature measurement of the upstream breathing gases) to determine an amount of water to add to the breathing gases to reach the desired humidity. In some cases, at calculate operation 1106, the processor of the humidifier may also calculate a temperature of a heating element for vaporizing the amount of water to be added to the breathing gases (or for maintaining the desired humidity in the breathing gases).

At optional second calculate operation 1107, when the water includes a dissolved medicine, a processor of the humidifier may calculate an amount of water including the dissolved medication. In this case, the amount of water may be calculated (above) to be sufficient to maintain the user-selected relative humidity of the breathing gases. Based on the amount of water and the concentration of the medicine, a second calculation may determine an amount of medicine that will be delivered to the breathing gases. As the amount of water may be required to maintain the user-selected humidity, a concentration of the medicine within the water may be adjusted to ensure delivery of a prescribed amount of the medicine. In some cases, when the medicine is infused into the water as it is pumped to the valve and/or atomizer, the infusion rate may automatically be adjusted based on the amount of water calculated in operation 1106 above. Other methods of determining and delivering an appropriate amount of medicine to the breathing gases may also be implemented, as known by one of skill in the art, and the above example is not intended to be limiting.

At control operation 1108, the humidifier controls an atomizer (and/or a valve) to deliver the amount of water (or water and medicine) calculated during operation 1106 (and optionally at operation 1107) to the breathing gases. In some aspects, at control operation 1108, the humidifier controls a valve to deliver the calculated amount of water in timed bursts of water to the atomizer, which delivers the calculated amount of water as small water droplets (e.g., in a hollow cone pattern) directly into the flow path of the breathing gases. For example the atomizer may be a hollow cone atomizer such as a pressure swirl atomizer. In some aspects, the valve may be a fast-response valve, such as fast-response solenoid valve, so that the calculated amount of water can be delivered in bursts or pulses to the atomizer. In further aspects, the humidifier during control operation 1108, controls the valve to deliver the calculated amount of water to the atomizer by adjusting a number and duration of the pulses during a predetermined delivery time.

In some aspects, a pump, such as a high pressure pump is fluidly connected between a water reservoir and the valve. In these aspects, upon opening of the valve, high pressure water is dispersed through the valve to the atomizer. For example, the high pressure water may have psi of greater than 50, 100, 200, 250, 300, 350, or 400 psi. In some aspects, the solenoid valve may be eliminated by using a pump that has a means of providing fast, well-timed, high pressure pulses of water to the atomizer upon an electrical command.

In some aspects, the humidifier at control operation 1108 delivers the calculated amount of water through a pressure swirl atomizer to the breathing gases. In these aspects, pressurized water may be ported to a single inlet channel in a distributor of the pressure swirl atomizer. The inlet channel directs the high-pressure water tangentially into a swirl chamber, resulting in a high velocity rotating fluid field in the swirl chamber. Because this rotating field is at high pressure relative to ambient, a vortex is created, causing the rapidly spinning water to be expelled out of the swirl chamber through a discharge orifice with high rotational velocity. The result is a spray of a “hollow cone” of very small water droplets. For example, the pressure swirl atomizer may produce cone angles (or average or mean cone angles) greater than 90 or 100 degrees, a film of water droplets (or a cone wall thickness) less than 0.1 mm, and/or water droplet sizes in the hollow cone of less than 10 microns. These characteristics of a high angle, very thin hollow cone of very small water droplets is what differentiates the pressure swirl atomizer from other types of atomizers.

At control operation 1110, the humidifier controls a heating element at a temperature (e.g., a temperature calculated at operation 1106) to vaporize the atomized water in the flow path downstream of the atomizer to form a humidified breathing gas. In some aspects, as described above, the heating element may be associated with a heating tube integrated in the humidifier; in other aspects, the heating element may be associated with a heating circuit including a heating inspiratory limb (and, in some cases, a heating exhalation limb). In further aspects, a heating element may be utilized in both a heating tube of the humidifier and a heating circuit. In examples, when the atomized water contacts the heating element (or a thermally-conductive material associated with the heating element), the water droplets vaporize to form gaseous water vapor. The gaseous water vapor may then diffuse in the breathing gases of the flow path to form a gaseous mixture of humidified breathing gases. In aspects, based on vaporizing the calculated amount of water, the humidified breathing gases are not over or under humidified and exhibit a desired humidity between 50% and 99% relative humidity (e.g., based on a user selection).

At determination operation 1112, the humidifier may receive different humidity information about the humidified breathing gases from a probe associated with a wye fitting of the ventilation tubing system. In this case, the different humidity information at the wye fitting may indicate that the humidified breathing gases are not at the desired humidity. If the humidifier receives different humidity information, the method may progress to recalculate operation 1114. If the humidifier does not receive different humidity information, the method may return to control operation 1108 and the humidifier may continue to deliver the calculated amount of water into the flow path of the breathing gases.

At recalculate operation 1114, a processor of the humidifier recalculates an amount of water to add to the breathing gases to reach the desired humidity based on the different humidity information. The humidifier during recalculate operation 1114 may also utilize the inspiratory flow information to determine an adjusted amount of water to add to the breathing gases to reach the desired humidity. In some cases, at calculate operation 1114, the processor of the humidifier may also recalculate a temperature of the heating element for vaporizing the adjusted amount of water to be added to the breathing gases (or for adjusting the temperature of the humidified breathing gases to reach the desired humidity). For example, based on the different humidity information, the humidifier may also control a temperature of the humidified breathing gases at the wye fitting to a user-selectable level in a range of, for example, 32 to 42 degrees C. Upon recalculating the amount of water and/or the temperature of the heating element, the method may return to control operation 1108 to vaporize the adjusted amount of water by controlling the heating element (which may also be controlled to an adjusted temperature).

After the breathing gas has been humidified at control operation 1110, the humidified breathing gases at the desired humidity may be delivered to the patient circuit for delivery to a patient being ventilated by the ventilator. In this way, method 1100 prevents or reduces over or under humidification of breathing gases.

In some aspects, a microprocessor-based ventilator or humidifier that accesses a computer-readable medium having computer-executable instructions for performing the method of humidifying ventilation breathing gas is disclosed. This method includes repeatedly performing the steps disclosed in method 1100 above and/or as illustrated in FIGS. 1-10A.

Those skilled in the art will recognize that the methods and systems of the present disclosure may be implemented in many manners and as such are not to be limited by the foregoing exemplary aspects and examples. In other words, functional elements being performed by a single or multiple components, in various combinations of hardware and software or firmware, and individual functions, can be distributed among software applications at either the client or server level or both. In this regard, any number of the features of the different aspects described herein may be combined into single or multiple aspects, and alternate aspects having fewer than or more than all of the features herein described are possible. Functionality may also be, in whole or in part, distributed among multiple components, in manners now known or to become known. Thus, myriad software/hardware/firmware combinations are possible in achieving the functions, features, interfaces and preferences described herein. Moreover, the scope of the present disclosure covers conventionally known manners for carrying out the described features and functions and interfaces, and those variations and modifications that may be made to the hardware or software firmware components described herein as would be understood by those skilled in the art now and hereafter.

Numerous other changes may be made which will readily suggest themselves to those skilled in the art and which are encompassed in the spirit of the disclosure and as defined in the appended claims. While various aspects have been described for purposes of this disclosure, various changes and modifications may be made which are well within the scope of the present disclosure. Numerous other changes may be made which will readily suggest themselves to those skilled in the art and which are encompassed in the spirit of the disclosure and as defined in the appended claims.

What is claimed is:

1. A method for humidifying ventilator delivered breathing gases, comprising:

receiving, at a humidifier, inspiratory flow information about breathing gases upstream of an atomizer of the humidifier;

measuring, by the humidifier, humidity information for the breathing gases upstream of the atomizer;

calculating, based on the inspiratory flow information and the humidity information, an amount of liquid to add to the breathing gases to reach a desired humidity;

delivering, via the atomizer, the amount of liquid in bursts of atomized liquid directly into a flow path of the breathing gases to form humidified breathing gases; and delivering the humidified breathing gases to a ventilation tubing system for delivery to a patient being ventilated.

2. The method of claim 1, further comprising vaporizing the atomized liquid upon contact of the liquid with a heating tube in the flow path downstream of the atomizer to form humidified breathing gases.

3. The method of claim 1, wherein the atomizer is a hollow cone atomizer.

4. The method of claim 3, wherein the hollow cone atomizer is a pressure swirl atomizer.

5. The method of claim 1, wherein the inspiratory flow information is received from a ventilator ventilating the patient.

6. The method of claim 1, wherein the inspiratory flow information is measured by a sensor associated with the humidifier.

7. The method of claim 1, wherein at least an inspiratory limb of the ventilation tubing system is heated.

8. The method of claim 1, wherein an inspiratory limb and an exhalation limb of the ventilation tubing system are heated.

9. The method of claim 1, further comprising:

receiving wye humidity information; and adjusting the amount of liquid to add to the breathing gases.

10. The method of claim 1, further comprising:

receiving, at the humidifier, a temperature measurement of the breathing gases upstream of the atomizer; and calculating, based on the inspiratory flow information, the humidity information, and the temperature measurement, the amount of liquid to add to the breathing gases to reach the desired humidity.

11. The method of claim 1, wherein the amount of liquid comprises a dissolved medicine at a concentration.

12. The method of claim 1, wherein the humidity information includes a temperature measurement and a relative humidity of the upstream breathing gases.

13. A humidifier that provides humidification to breathing gases for ventilating a patient, comprising:

an atomizer;

a first sensor that monitors an inspiratory flow of breathing gases upstream of an atomizer of the humidifier;

a second sensor that monitors humidity information of the breathing gases upstream of the atomizer;

a processor that calculates, based on the inspiratory flow and the humidity information, an amount of water to add to the breathing gases to reach a desired humidity; and a controller that commands the atomizer to deliver the amount of liquid in bursts of atomized liquid directly into a flow path of the breathing gases.

14. The humidifier of claim 13, wherein the controller further commands a heating element to heat a thermally conductive material in the flow path downstream of the atomizer, wherein the atomized liquid is vaporized upon contact with the thermally conductive material.

15. The humidifier of claim 14, wherein the heating element is associated with a heating circuit comprising the thermally conductive material, and wherein the heating circuit is located downstream of the humidifier.

16. The humidifier of claim 15, wherein the atomizer is a first atomizer and the humidifier further comprises a second atomizer for delivering a second liquid.

17. The humidifier of claim 16, wherein the second atomizer is positioned downstream of the first atomizer and the thermally conductive material.

18. The humidifier of claim 13, wherein the first sensor is downstream from the second sensor.

19. A humidifier that provides humidification to breathing gases for ventilating a patient, comprising:

a controller that receives inspiration flow information about an inspiratory flow of breathing gases upstream of the humidifier;

a processor that calculates, based on the inspiratory flow, an amount of liquid to add to the breathing gases;

an atomizer commanded by the controller to deliver the amount of water in bursts of atomized water directly into a flow path of the breathing gases; and a heating element commanded by the controller to heat a thermally conductive material in the flow path downstream of the atomizer.

20. The humidifier of claim 19, wherein the heating element is associated with a heating tube comprising the thermally conductive material, and wherein the heating tube is located downstream of the atomizer within the humidifier.

* * * * *